(12) United States Patent
Kwokal et al.

(10) Patent No.: US 8,722,722 B2
(45) Date of Patent: May 13, 2014

(54) RALTEGRAVIR SALTS AND CRYSTALLINE FORMS THEREOF

(71) Applicant: Teva Pharmaceuticals USA, Inc., Petah Tigva, PA (US)

(72) Inventors: Ana Kwokal, Zagreb (HR); Lilach Hedvati, Doar Na Hefer (IL); Revital Burstein, Ramat-Hasharon (IL); Adi Yeori, Tel Aviv (IL); Rinat Moshkovits-Kaptsan, Raanana (IL)

(73) Assignee: Teva Pharmaceutical Industries Ltd, Petah Tiqva, IL (US)

( * ) Notice: Subject to any disclaimer, the term of this patent is extended or adjusted under 35 U.S.C. 154(b) by 0 days.

(21) Appl. No.: 13/708,141

(22) Filed: Dec. 7, 2012

(65) Prior Publication Data
US 2013/0096147 A1   Apr. 18, 2013

Related U.S. Application Data

(63) Continuation of application No. 13/637,497, filed as application No. PCT/US2011/030892 on Apr. 1, 2011.

(60) Provisional application No. 61/320,062, filed on Apr. 1, 2010, provisional application No. 61/326,922, filed on Apr. 22, 2010, provisional application No. 61/329,284, filed on Apr. 29, 2010, provisional application No. 61/353,398, filed on Jun. 10, 2010, provisional application No. 61/392,770, filed on Oct. 13, 2010, provisional application No. 61/392,759, filed on Oct. 13, 2010, provisional application No. 61/417,632, filed on Nov. 29, 2010.

(51) Int. Cl.
| | |
|---|---|
| *A01N 43/48* | (2006.01) |
| *A01N 43/42* | (2006.01) |
| *A01N 43/54* | (2006.01) |
| *A61K 31/505* | (2006.01) |
| *A61K 31/47* | (2006.01) |
| *A61K 31/40* | (2006.01) |

(52) U.S. Cl.
USPC .................. 514/411; 514/269; 514/319

(58) Field of Classification Search
None
See application file for complete search history.

(56) References Cited

U.S. PATENT DOCUMENTS

| | | |
|---|---|---|
| 7,169,780 B2 | 1/2007 | Crescenzi et al. |
| 7,754,731 B2 | 7/2010 | Belyk et al. |
| 2006/0122205 A1* | 6/2006 | Belyk et al. ............ 514/269 |

FOREIGN PATENT DOCUMENTS

| | | |
|---|---|---|
| WO | WO 2006/060681 | 6/2006 |
| WO | WO 2010/140156 | 12/2010 |
| WO | WO 2011/024192 | 3/2011 |

OTHER PUBLICATIONS

Brittain, "Polymorphism in Pharmaceutical Solids", 1999, Marcel Dekker, Inc., New York, NY, 232-239, (Swarbrick), "Drugs and the Pharmaceutical Sciences" 4 pages.
International Search Report for International Application No. PCT/US2011/030892, mailed on Aug. 18, 2011.
Written Opinion of the International Searching Authority for International Application No. PCT/US2011/030892, mailed on Aug. 18, 2011.
International Preliminary Report on Patentability for International Application No. PCT/US2011/030892, issued on Oct. 2, 2012.

* cited by examiner

*Primary Examiner* — Craig Ricci
*Assistant Examiner* — Jared D Barsky
(74) *Attorney, Agent, or Firm* — Baker & Hostetler LLP

(57) ABSTRACT

The present invention includes new salts of Raltegravir and crystalline forms thereof, pharmaceutical compositions containing the salts or crystalline forms, methods of using the salts or crystalline forms or the compositions to treat HIV infection or to prepare medicament for treating HIV infection, and a process for preparing Raltegravir potassium.

7 Claims, 36 Drawing Sheets

FIGURES
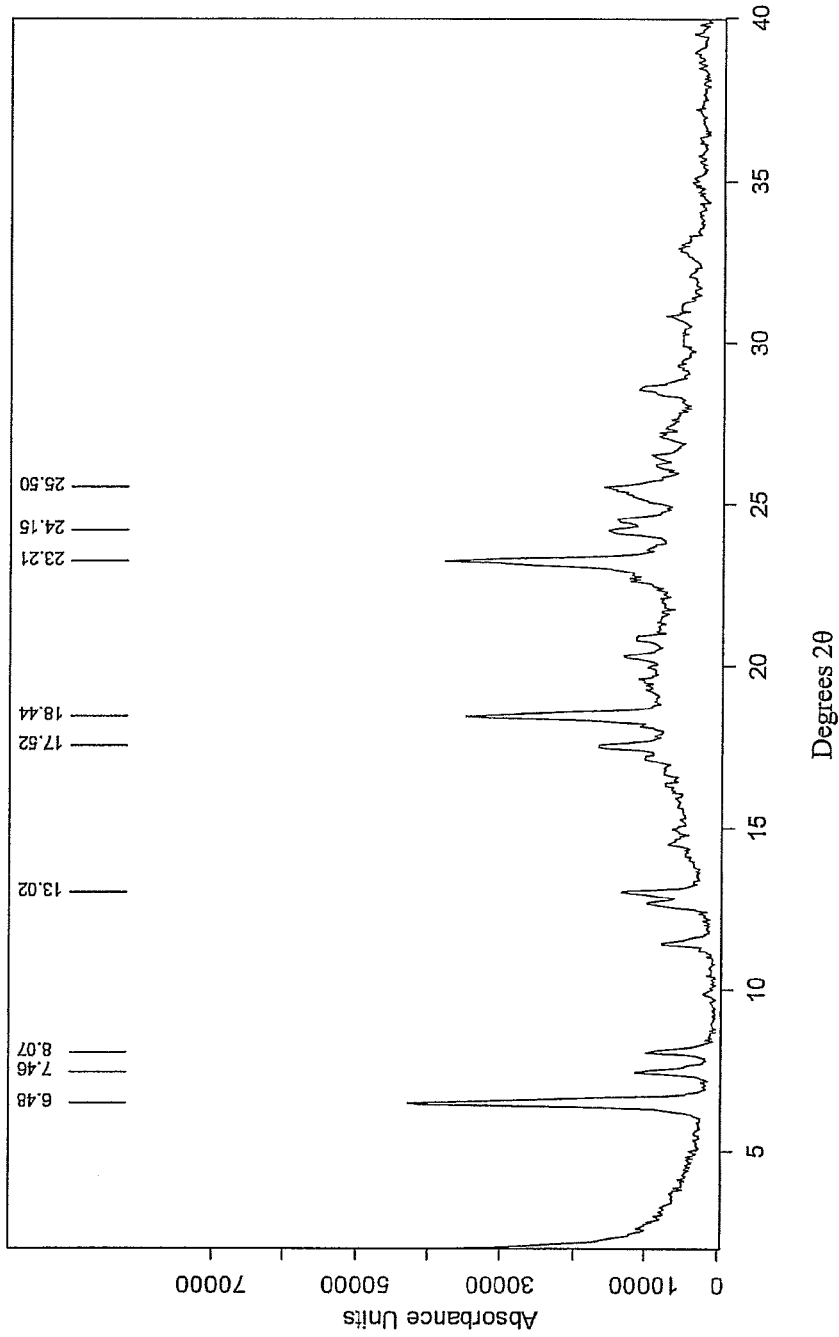
Figure 1: A characteristic X-ray powder diffractogram of Raltegravir potassium Form IV.

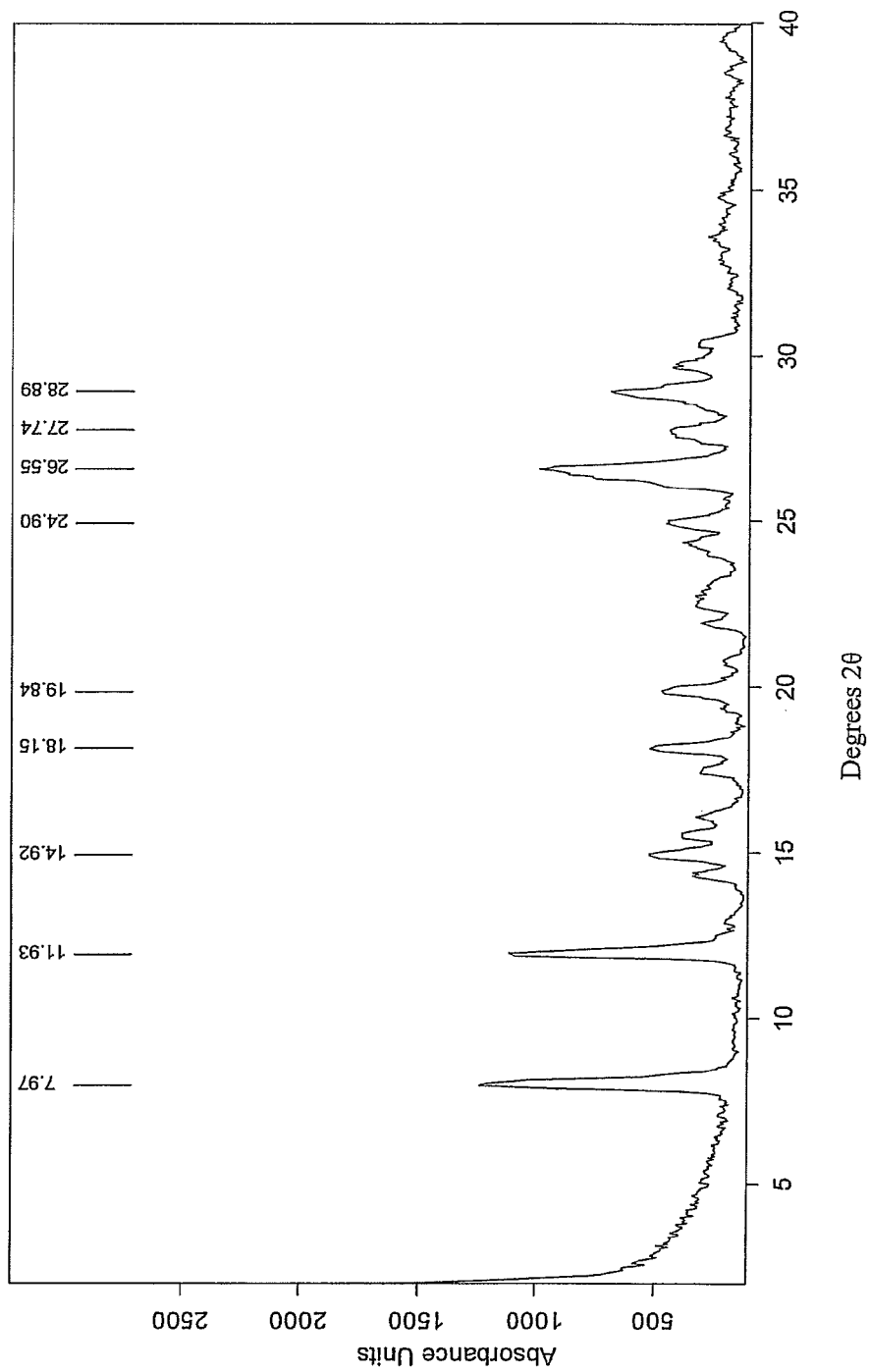
Figure 2: A characteristic X-ray powder diffractogram of Raltegravir potassium Form V.

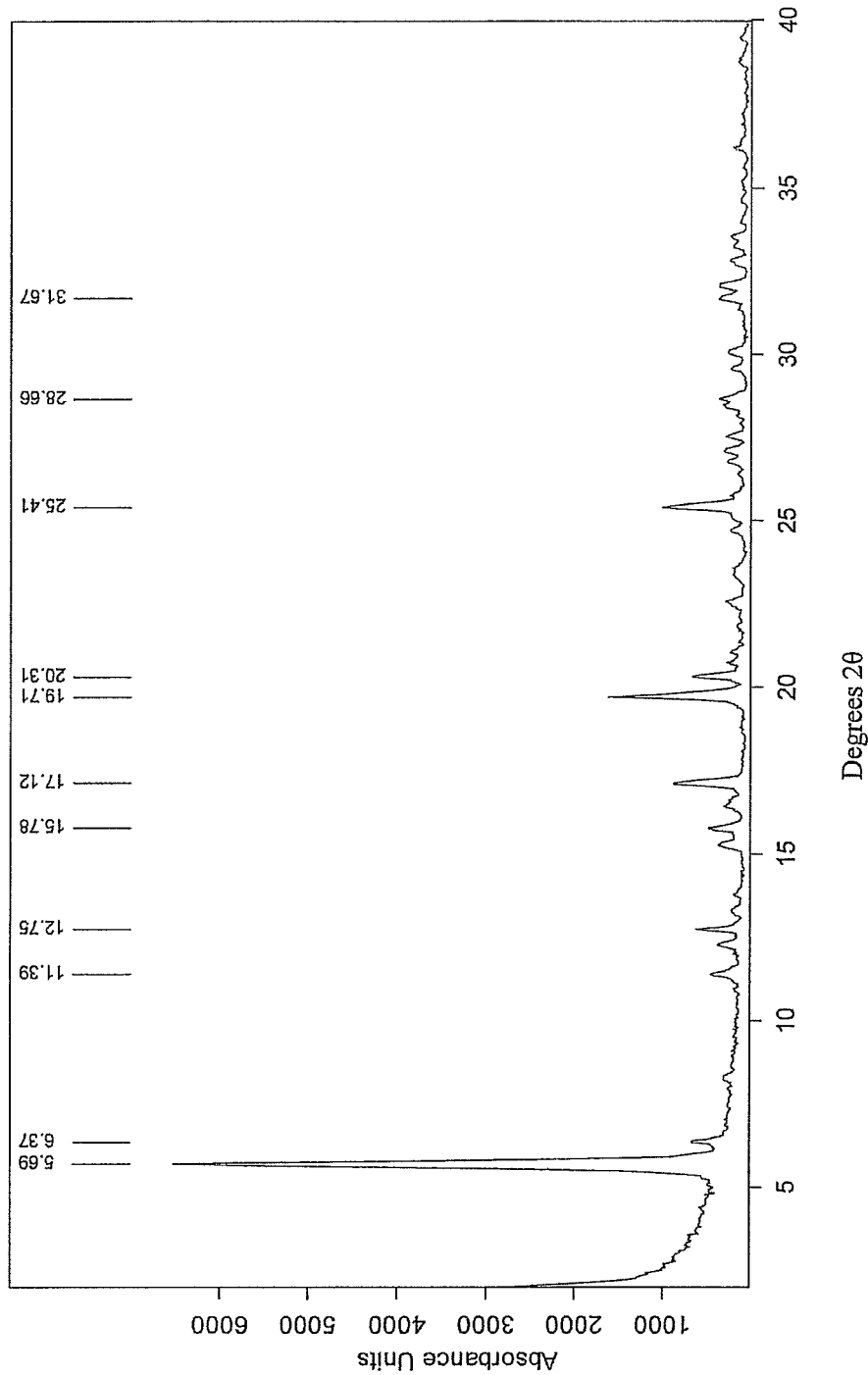
Figure 3: A characteristic X-ray powder diffractogram of Raltegravir potassium Form VI.

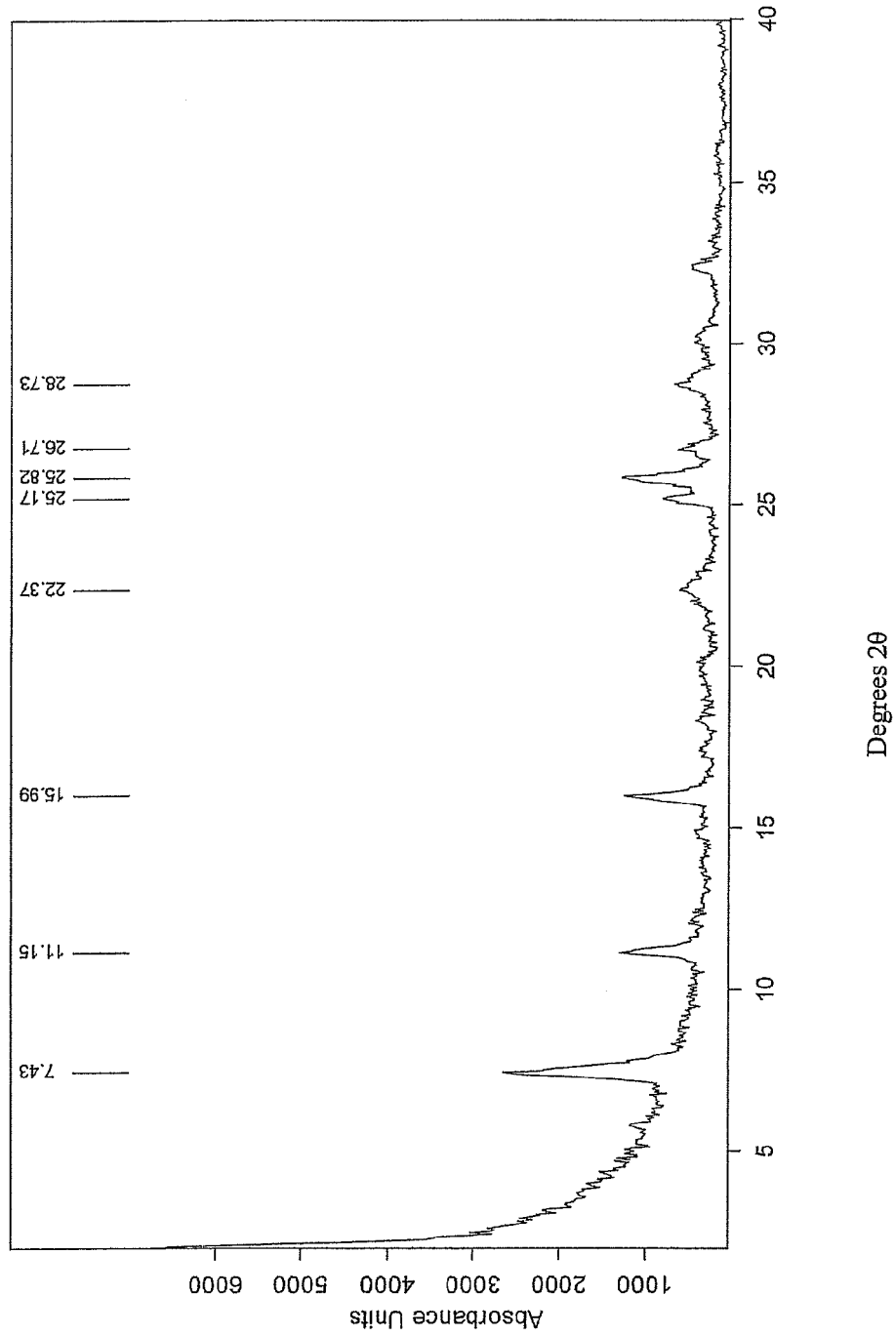
Figure 4: A characteristic X-ray powder diffractogram of Raltegravir potassium Form VII.

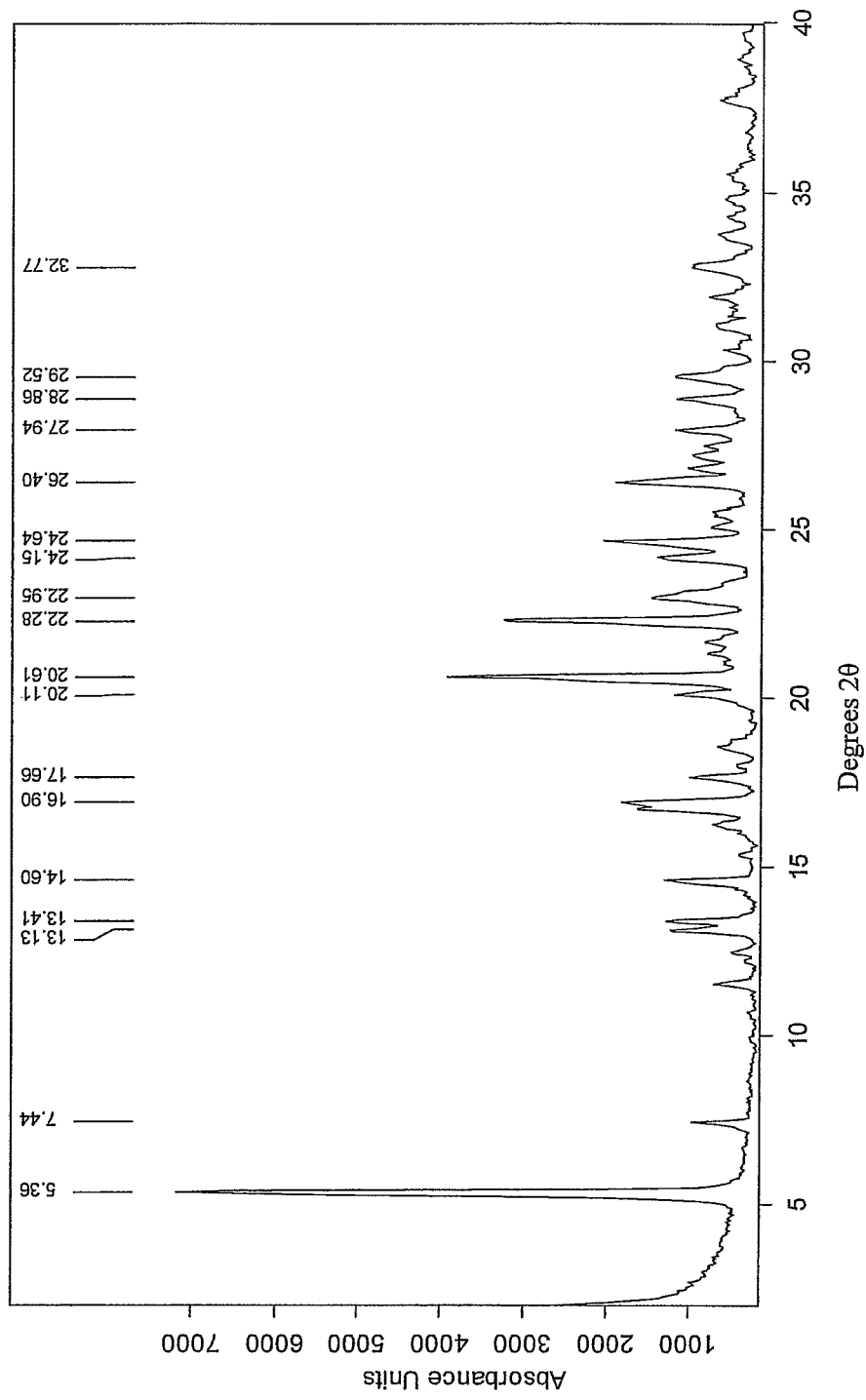
Figure 5: A characteristic X-ray powder diffractogram of Raltegravir potassium Form VIII.

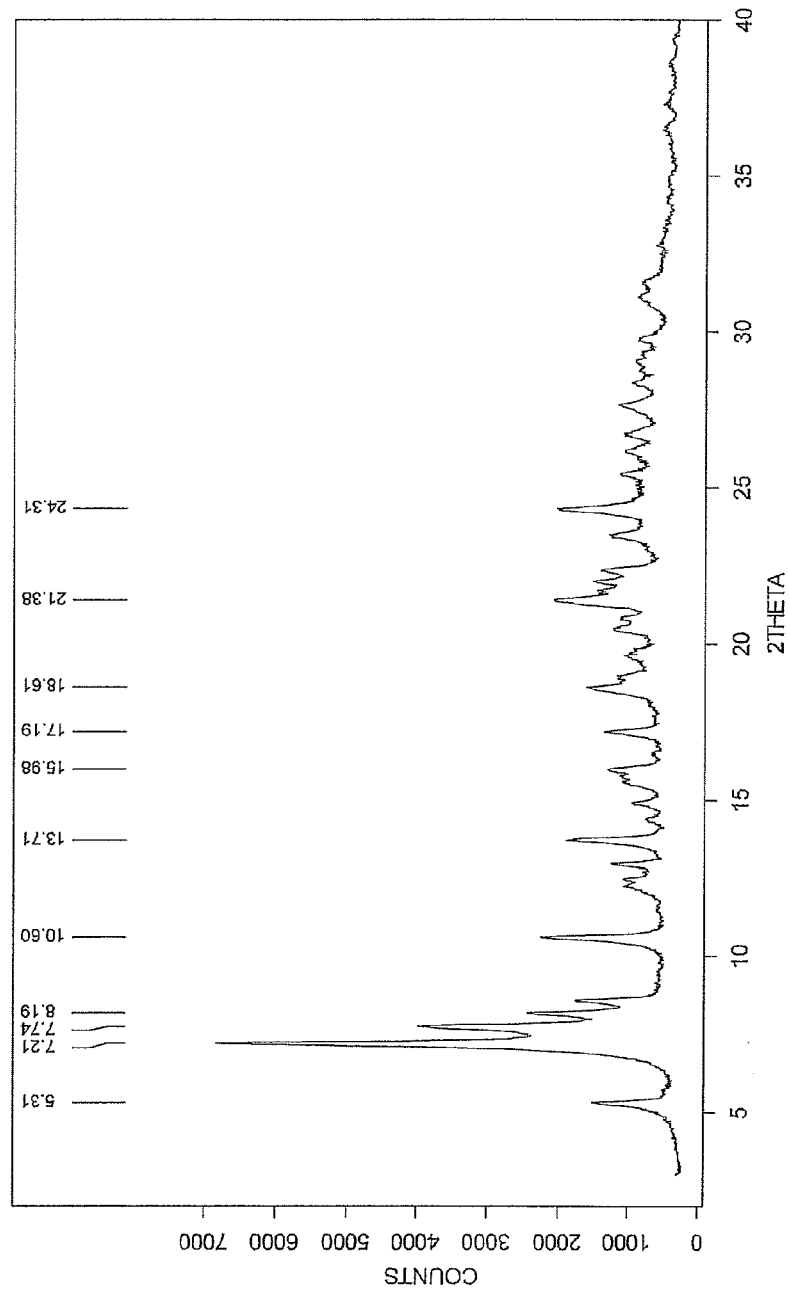
Figure 6: A characteristic X-ray powder diffractogram of Raltegravir potassium Form IXa.

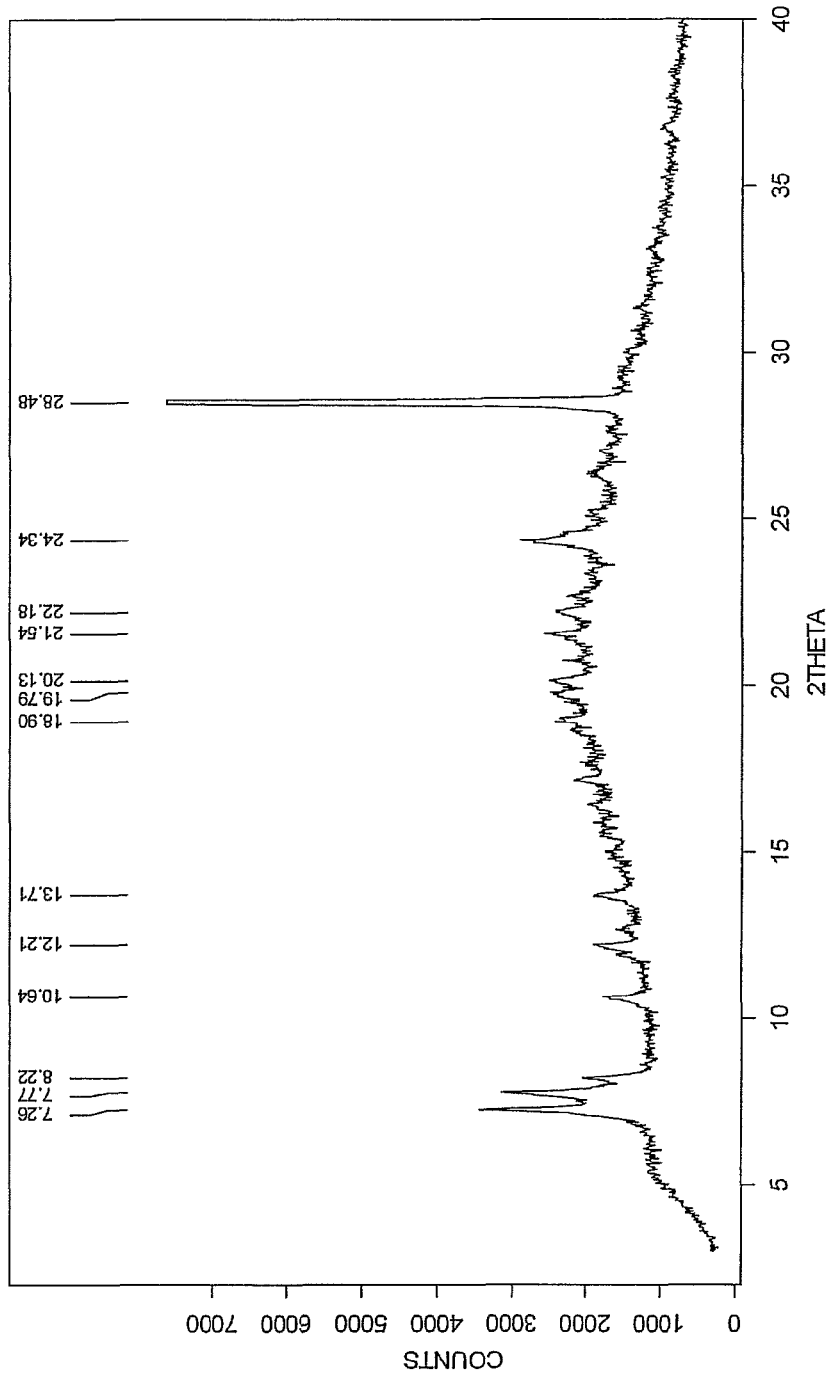
Figure 7: A characteristic X-ray powder diffractogram of Raltegravir potassium Form IXb.
* The peak at 28.48 corresponds to silicon powder (Si).

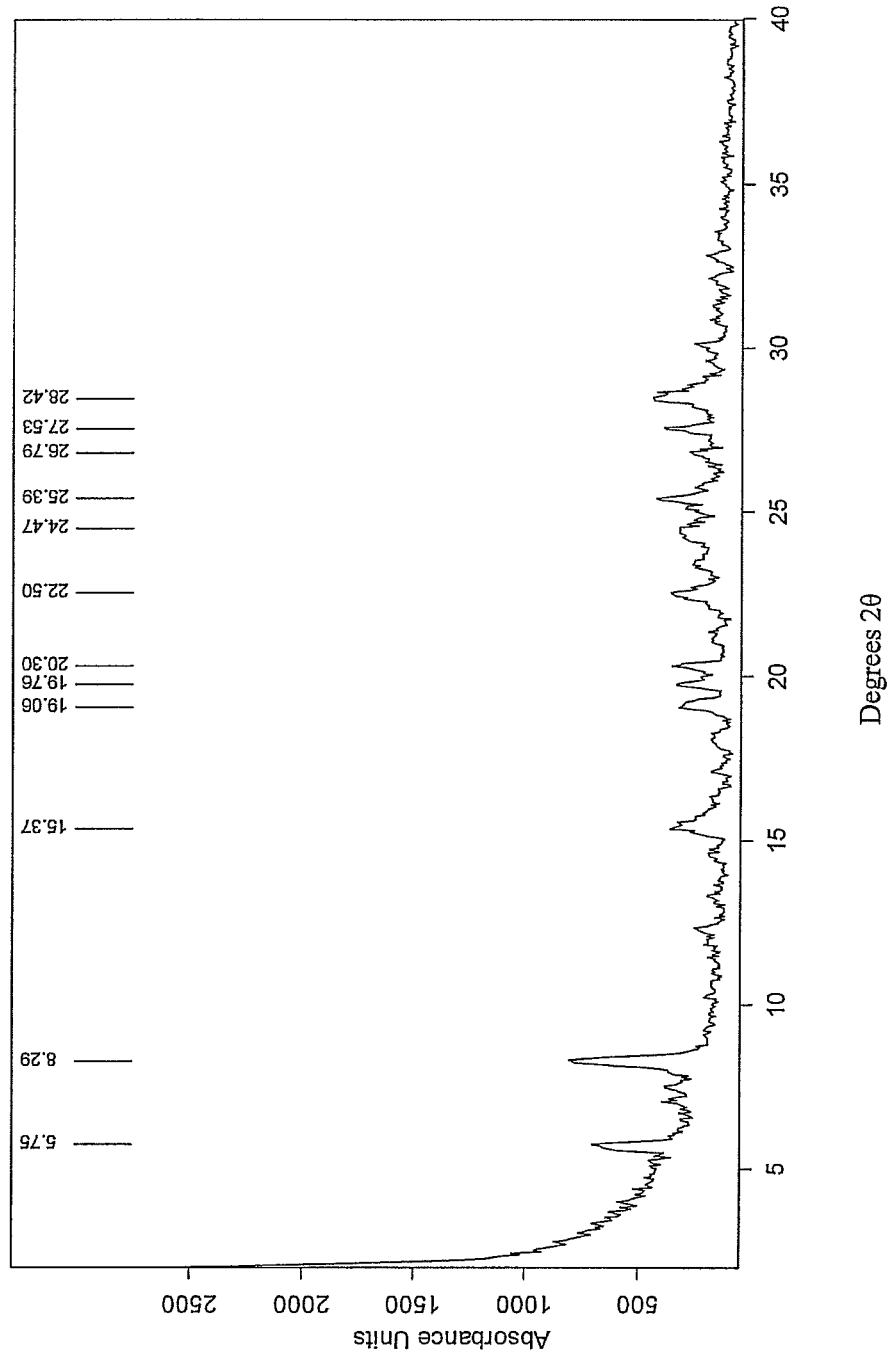
Figure 8: A characteristic X-ray powder diffractogram of Raltegravir potassium Form X.

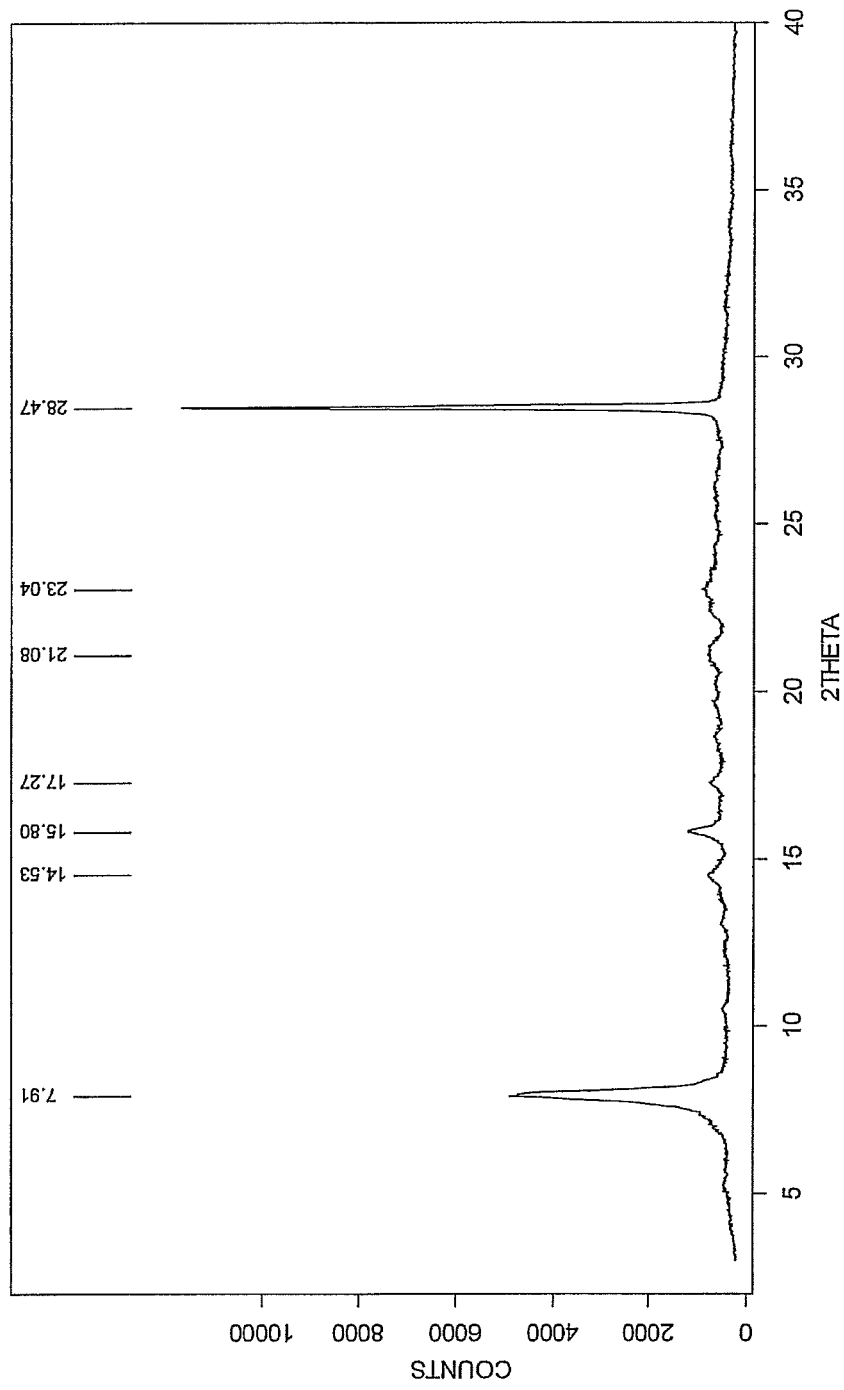
Figure 9: A characteristic X-ray powder diffractogram of Raltegravir potassium Form XI.
* The peak at 28.47 corresponds to silicon powder (Si).

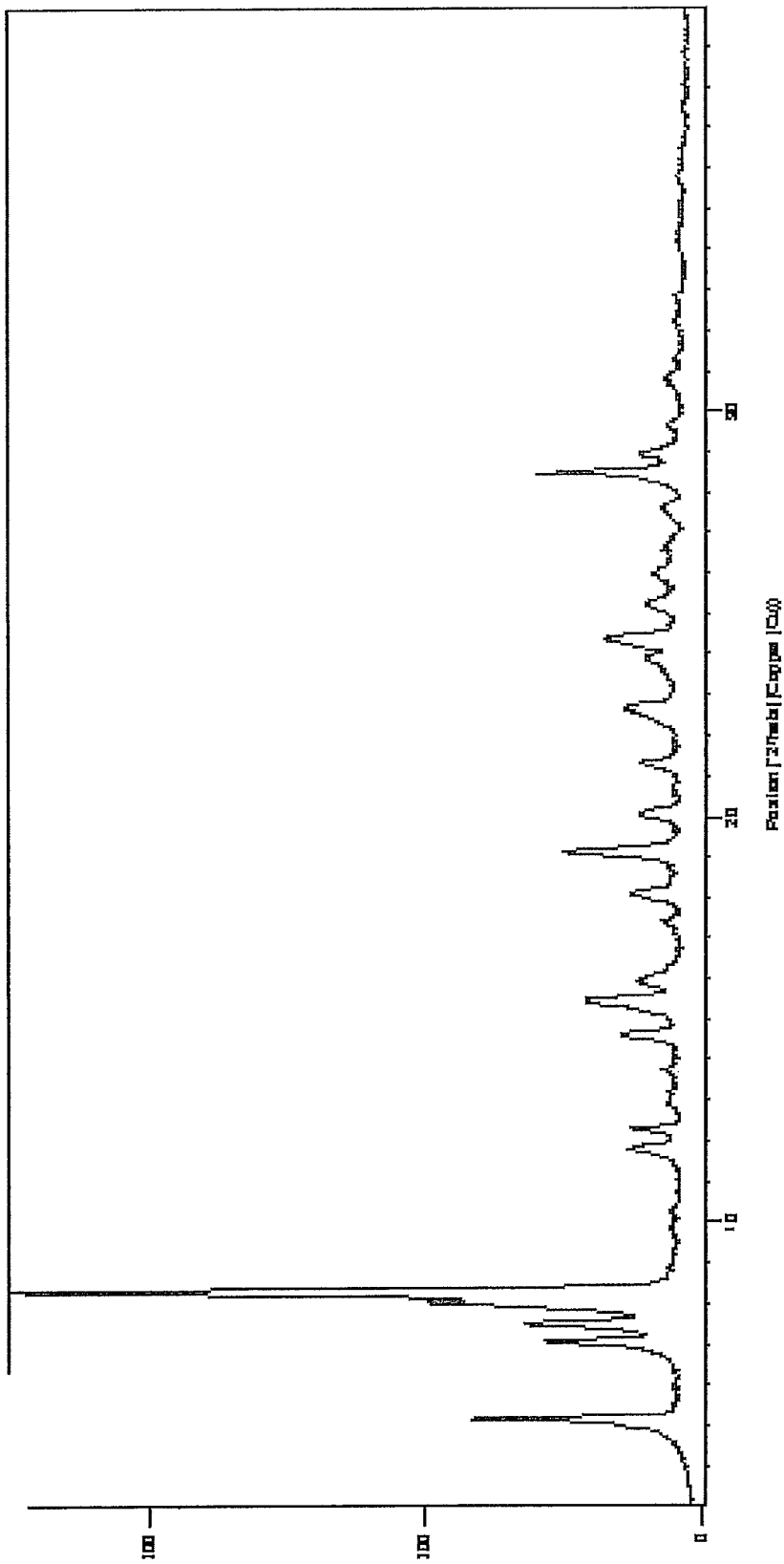
Figure 10: A characteristic X-ray powder diffractogram of Raltegravir potassium Form XII.

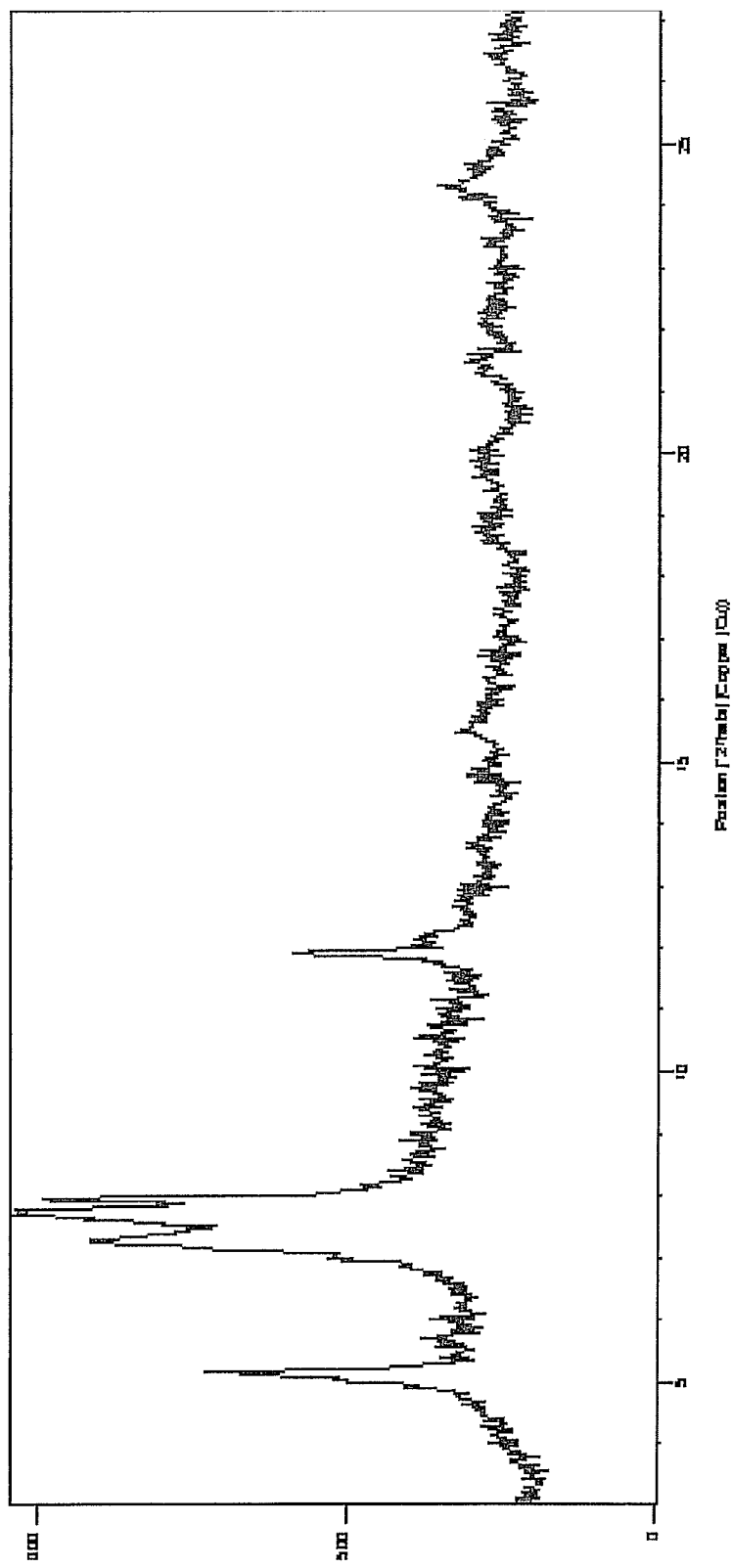
Figure 11: A characteristic X-ray powder diffractogram of Raltegravir potassium Form XIII.

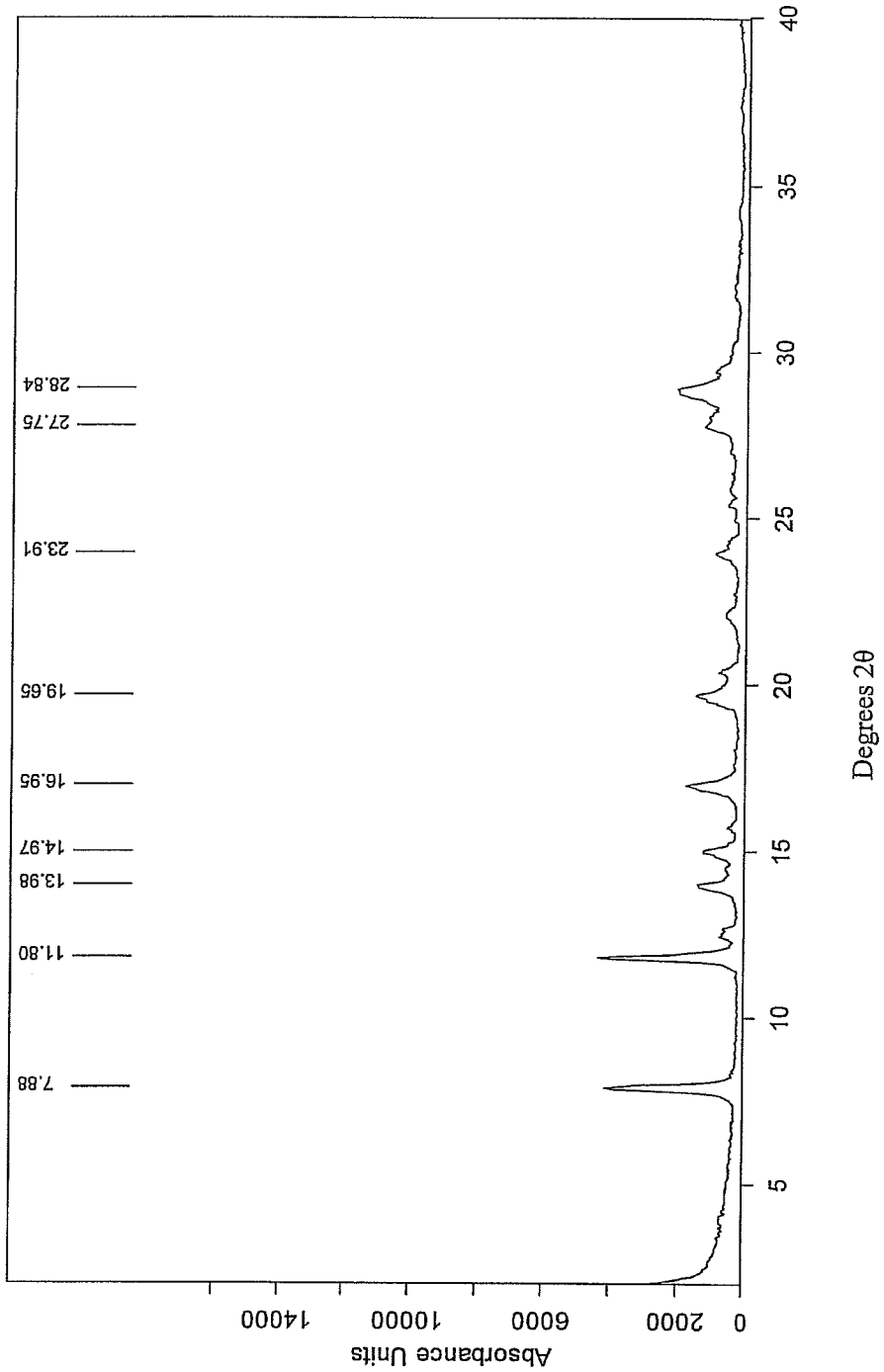
Figure 12: A characteristic X-ray powder diffractogram of Raltegravir sodium Form S1.

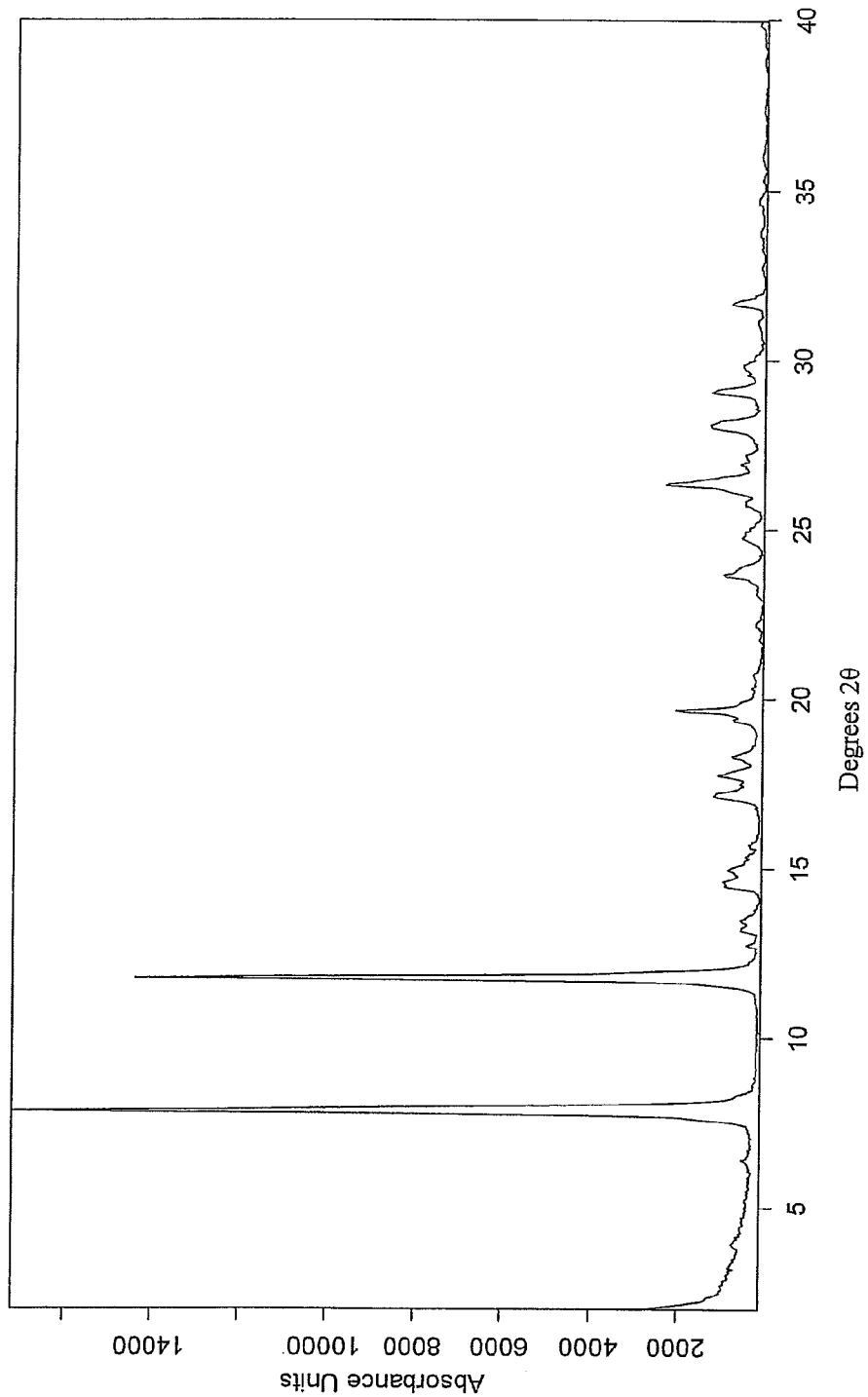
Figure 13: A characteristic X-ray powder diffractogram of Raltegravir sodium Form S2.

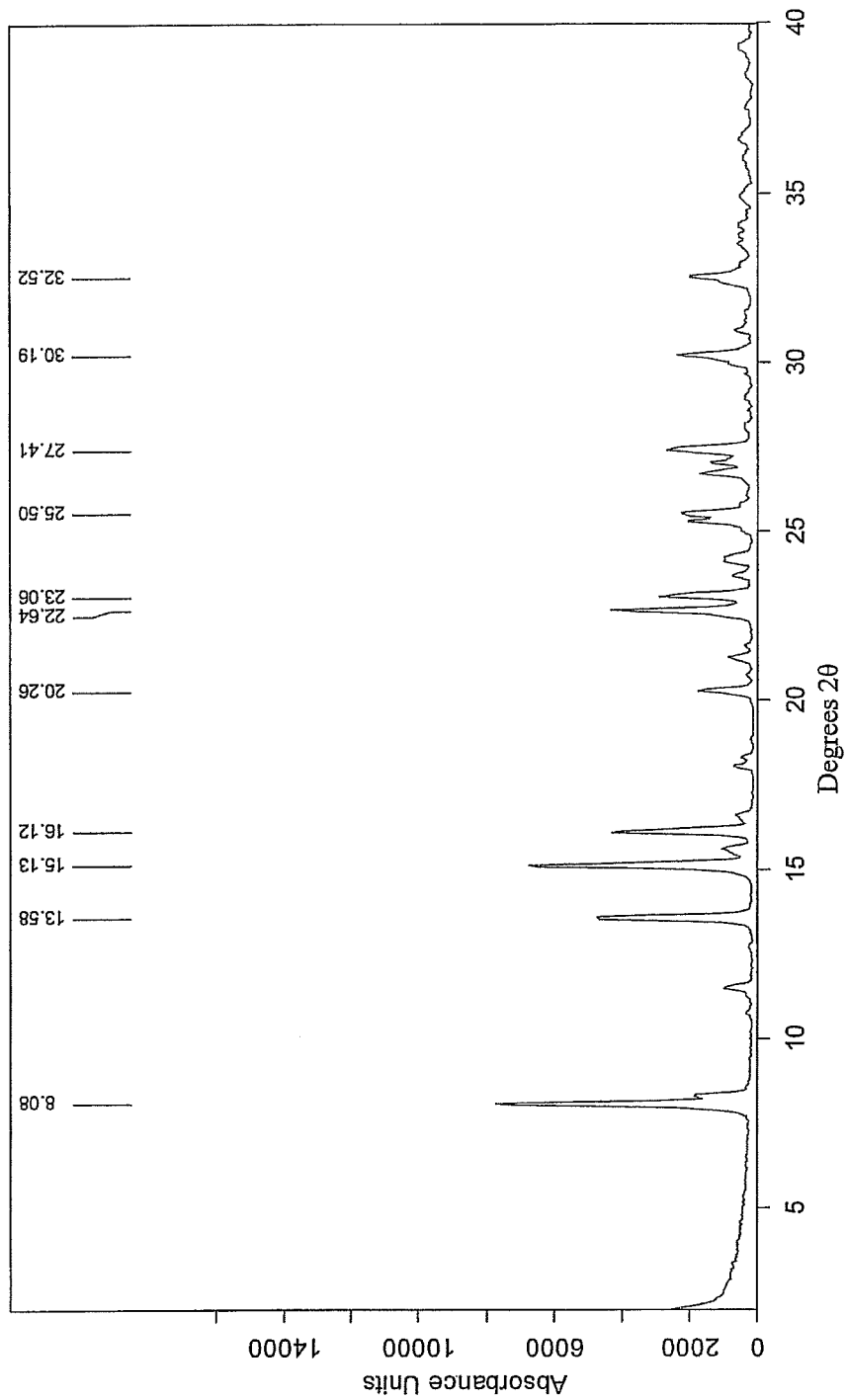
Figure 14: A characteristic X-ray powder diffractogram of Raltegravir sodium Form S3.

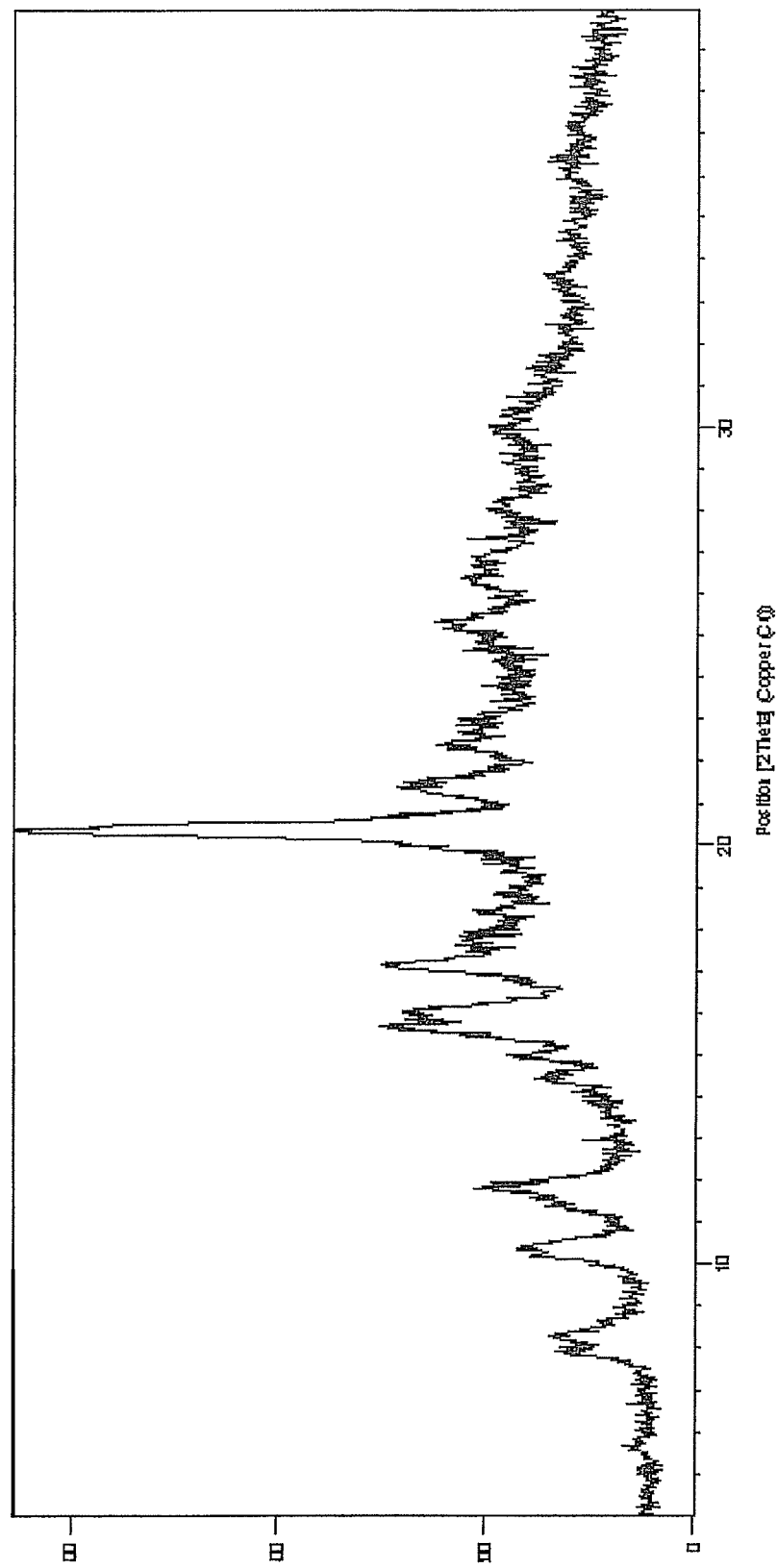
Figure 15: A characteristic X-ray powder diffractogram of Raltegravir lithium salt.

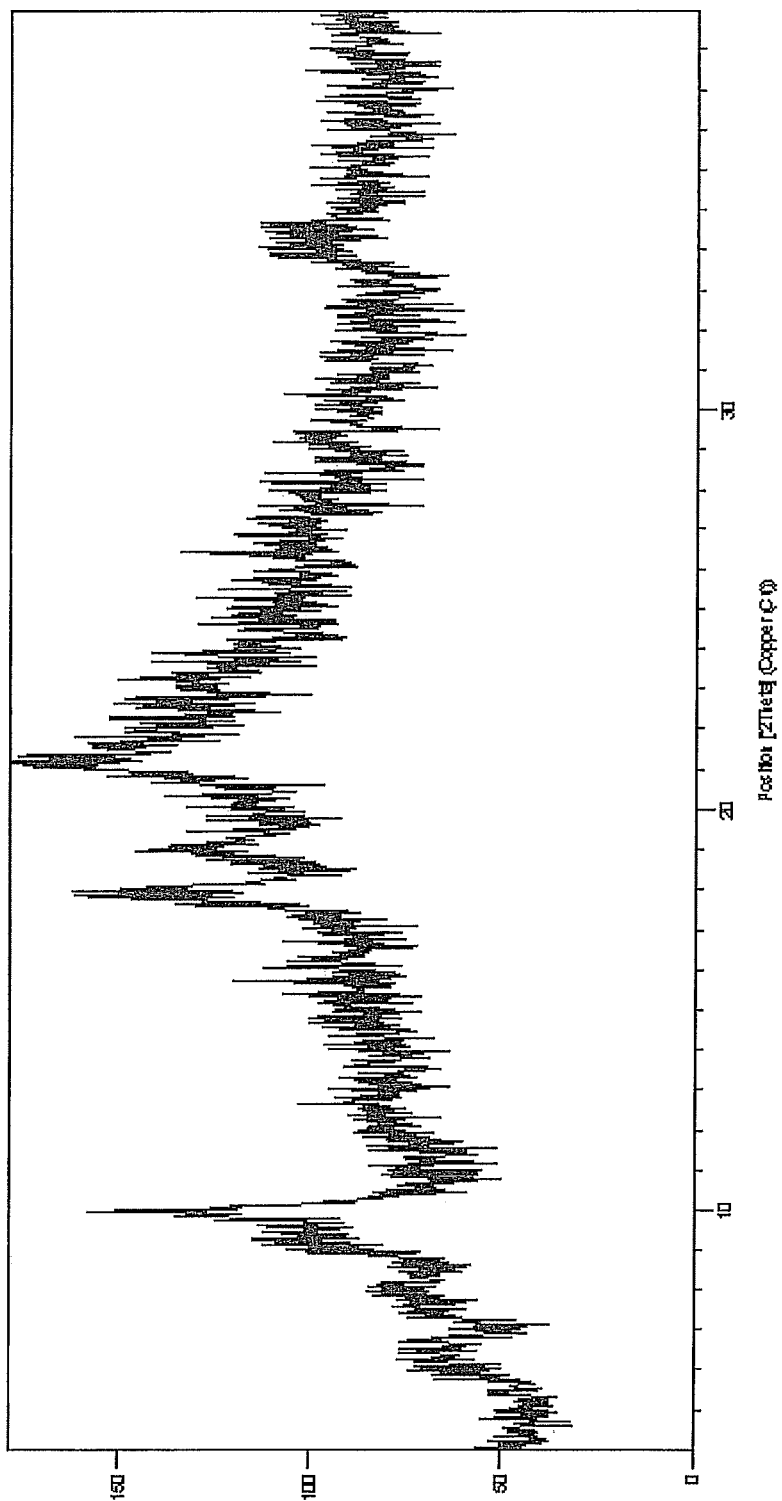
Figure 16: A characteristic X-ray powder diffractogram of Raltegravir calcium salt.

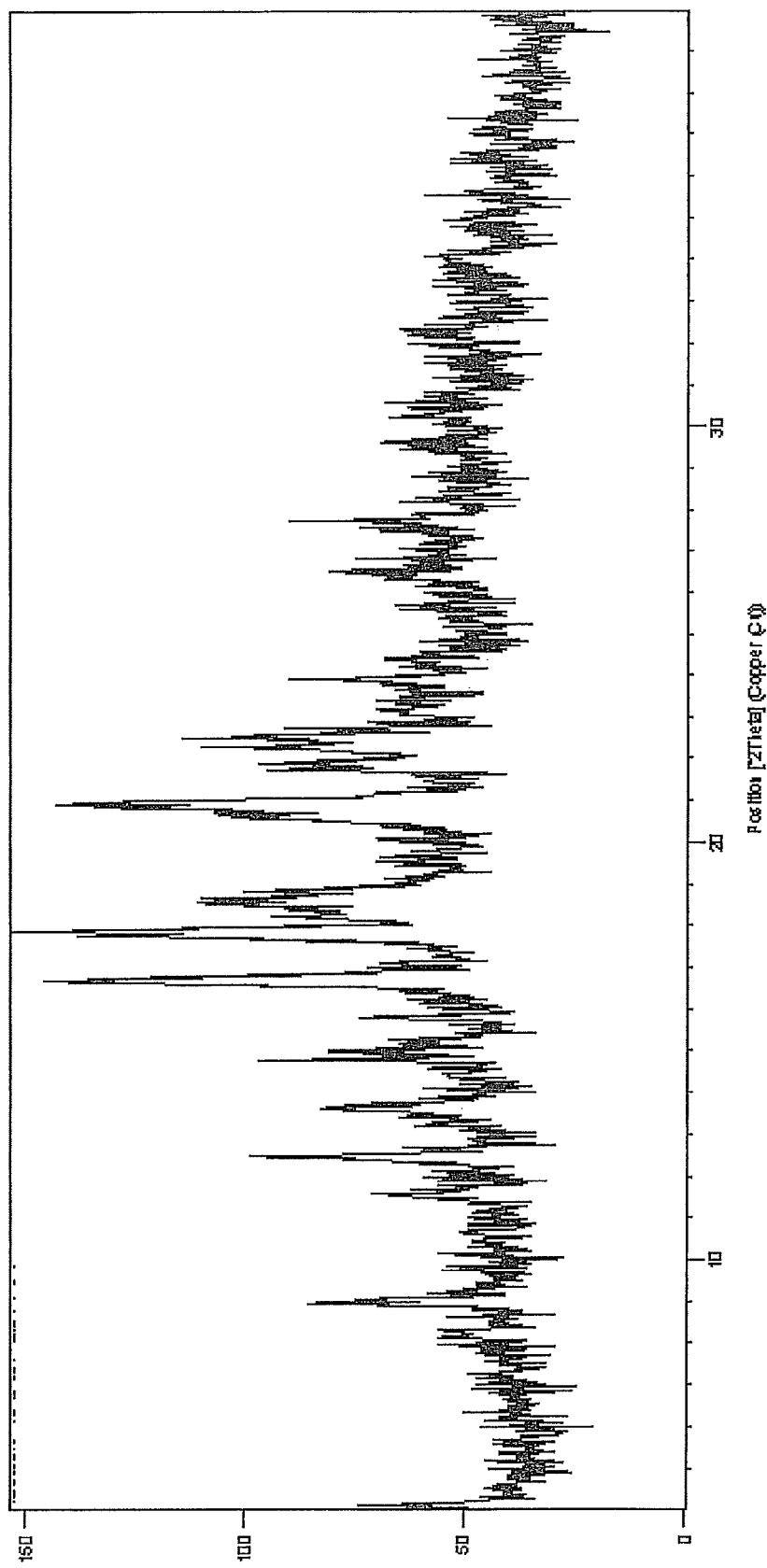
Figure 17: A characteristic X-ray powder diffractogram of Raltegravir *tert*-butylamine salt.

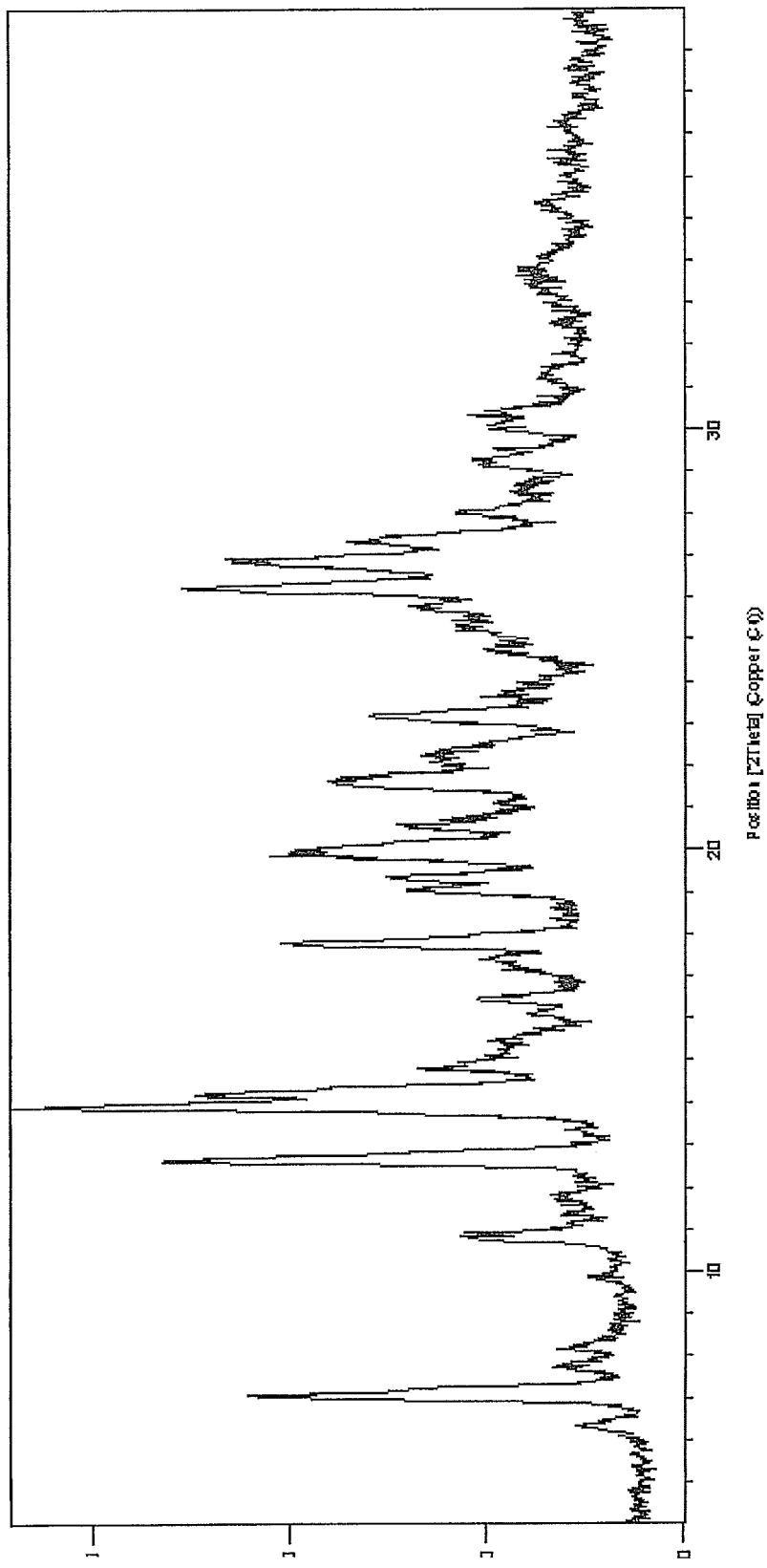
Figure 18: A characteristic X-ray powder diffractogram of Raltegravir diethylamine salt.

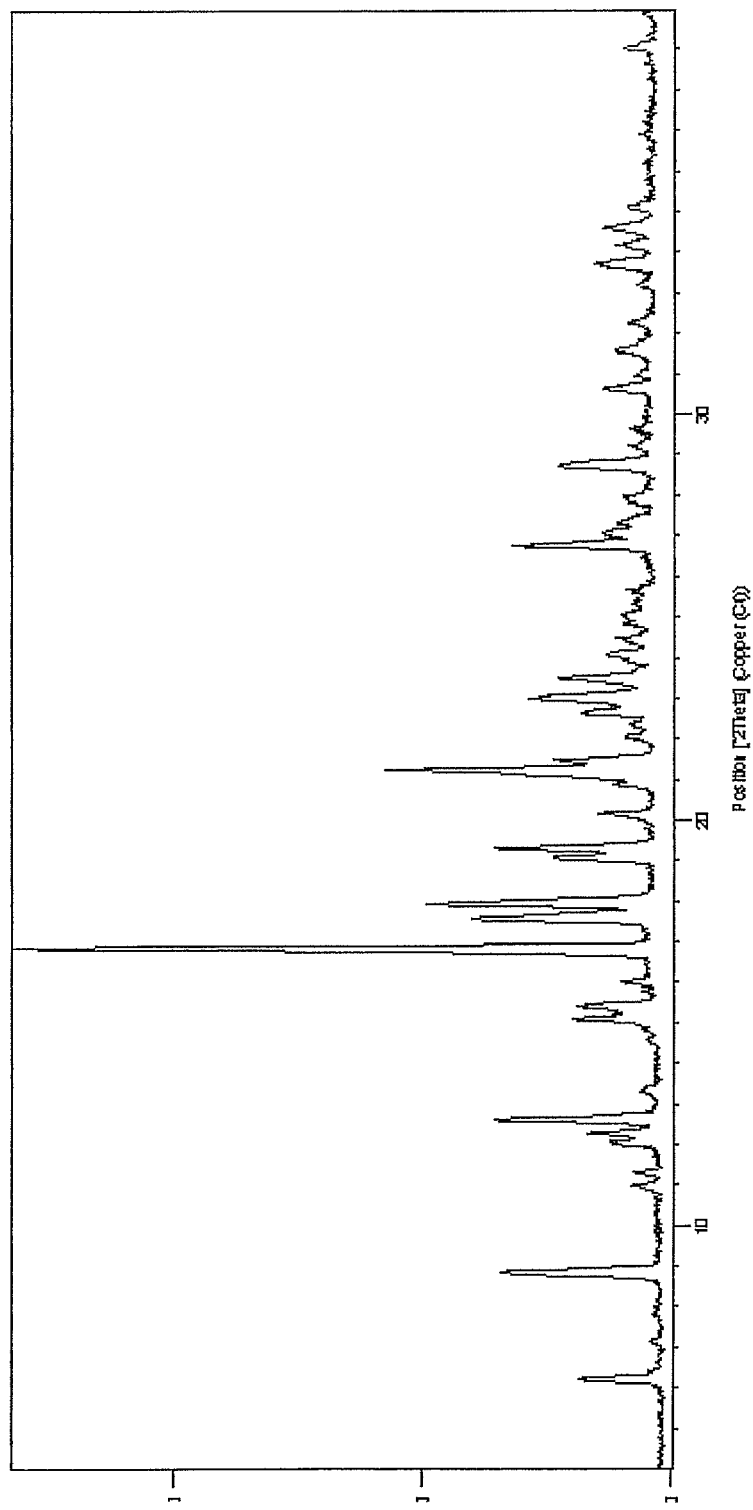
Figure 19: A characteristic X-ray powder diffractogram of Raltegravir diisopropylamine salt.

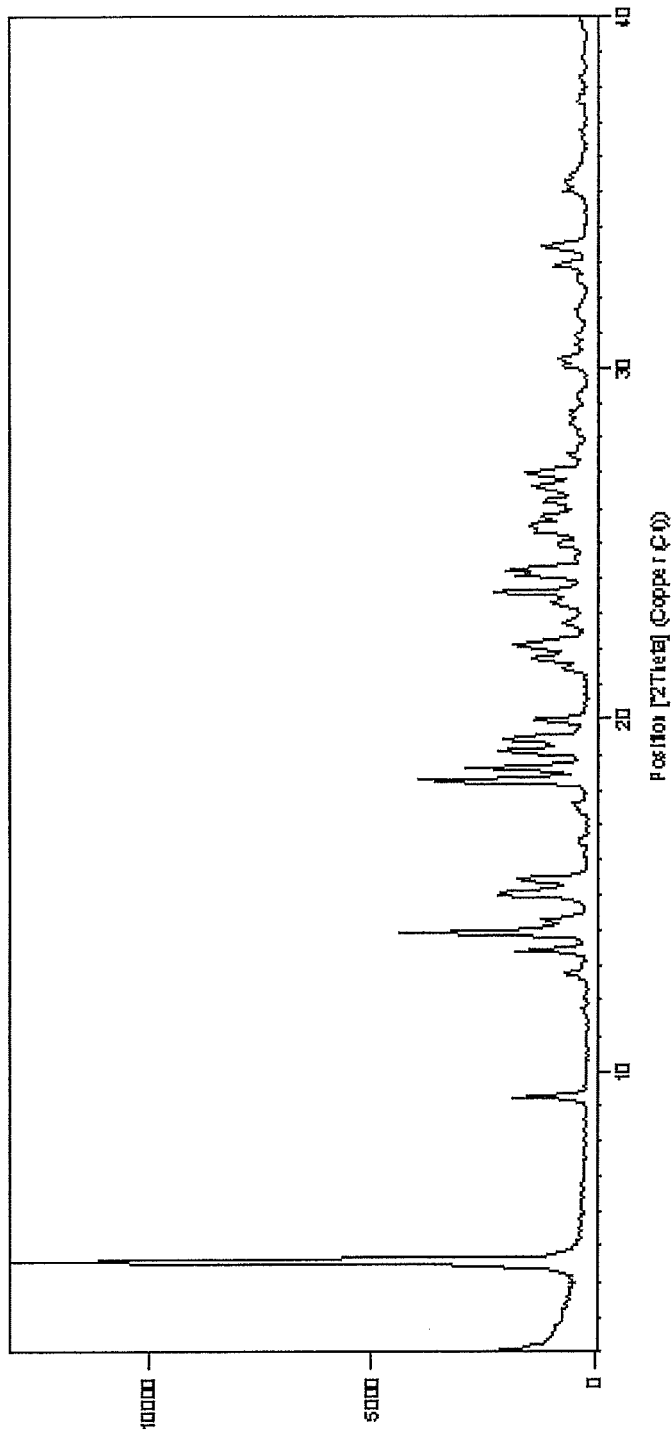
Figure 20: A characteristic X-ray powder diffractogram of Raltegravir potassium Form XIV.

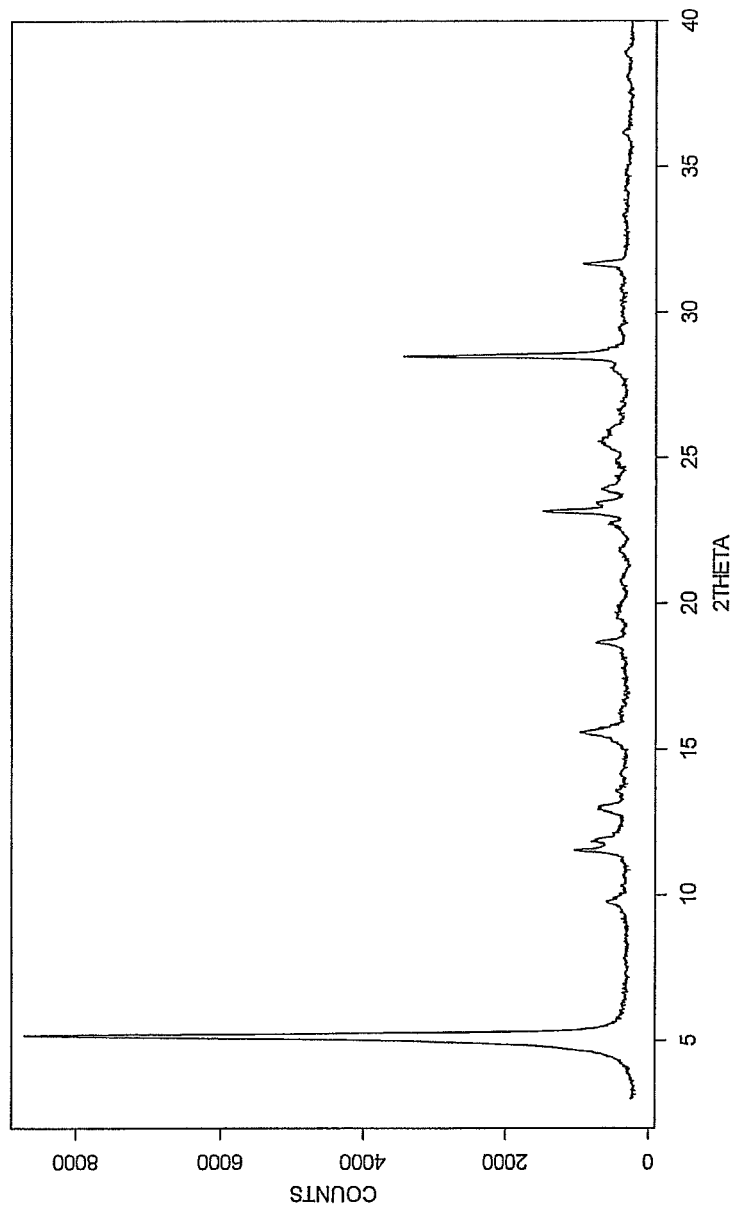
Figure 21: A characteristic X-ray powder diffractogram of Raltegravir potassium Form XV
* The peak at 28.5 corresponds to silicon powder (Si).

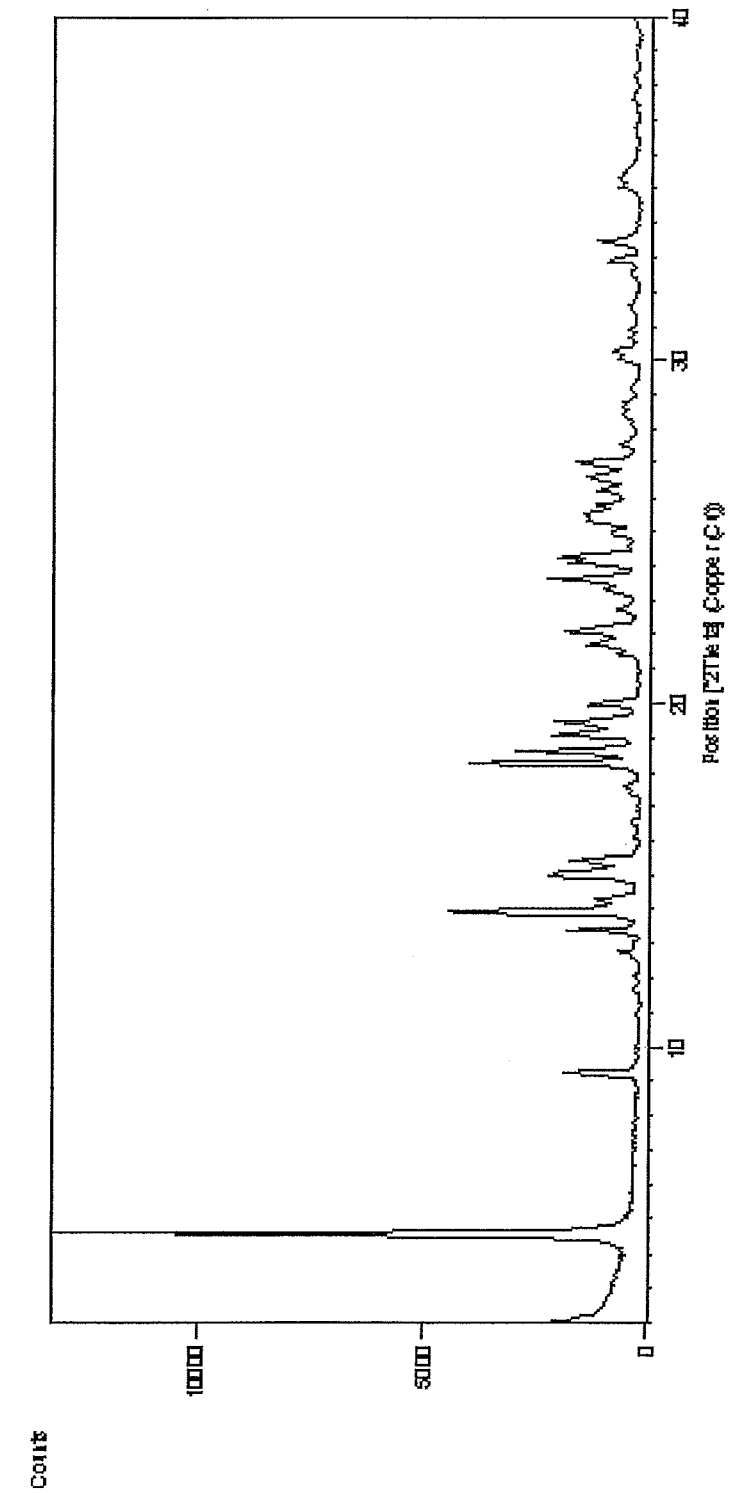
Figure 22: A characteristic X-ray powder diffractogram of Raltegravir potassium Form XVI.

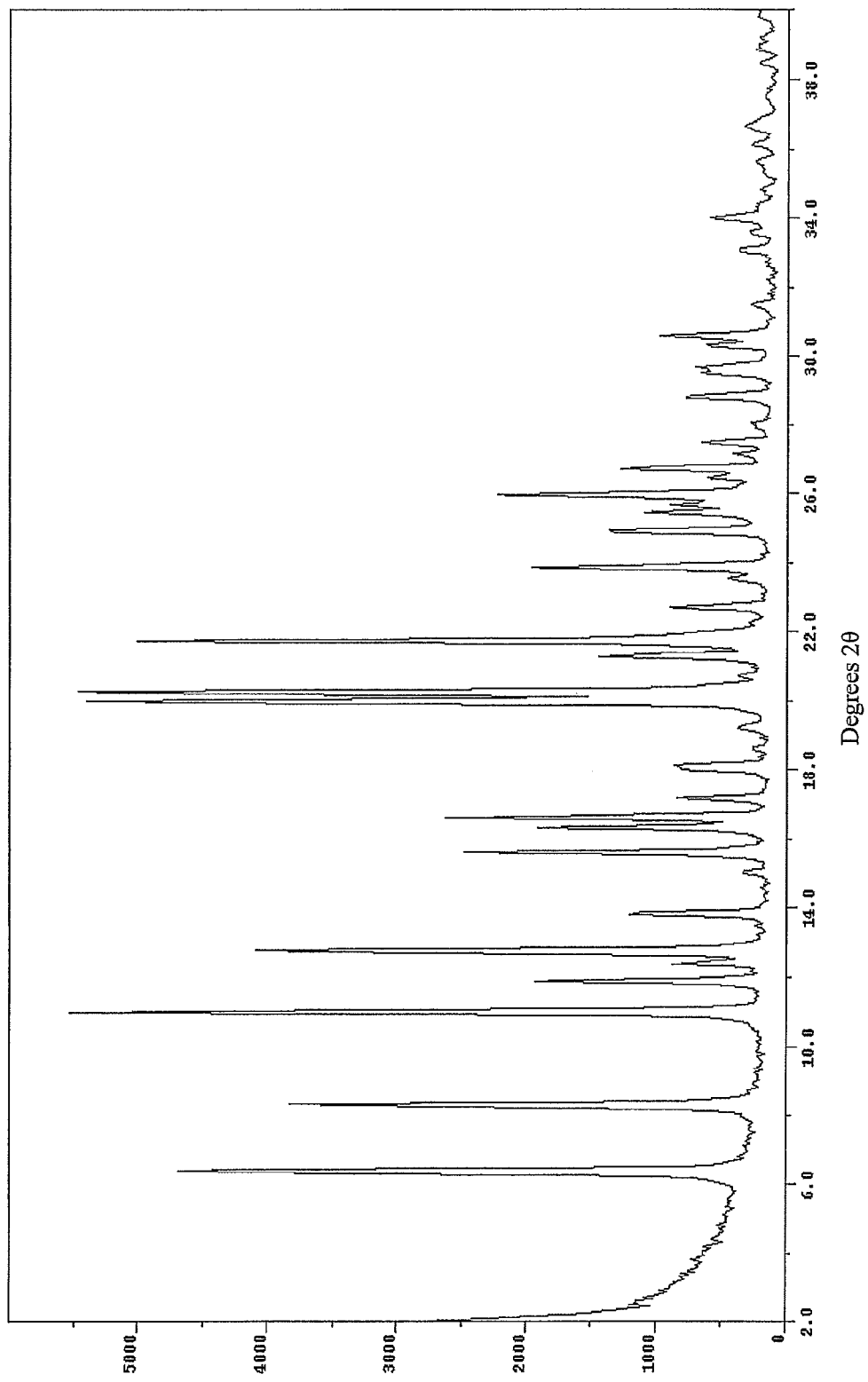
Figure 23: A characteristic X-ray powder diffractogram of Raltegravir free hydroxy Form A1

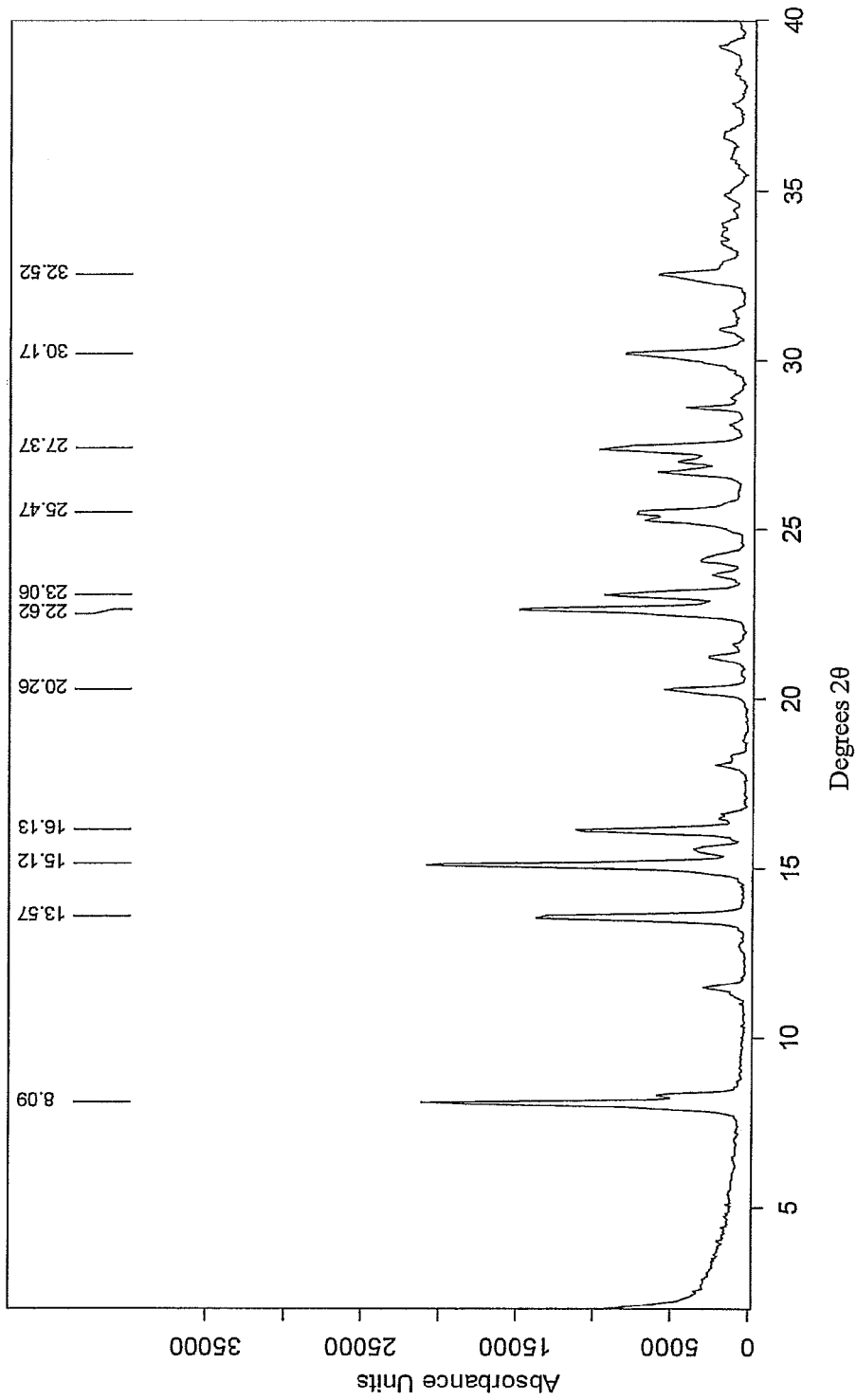
Figure 24: A characteristic X-ray powder diffractogram of Raltegravir free hydroxy Form A2

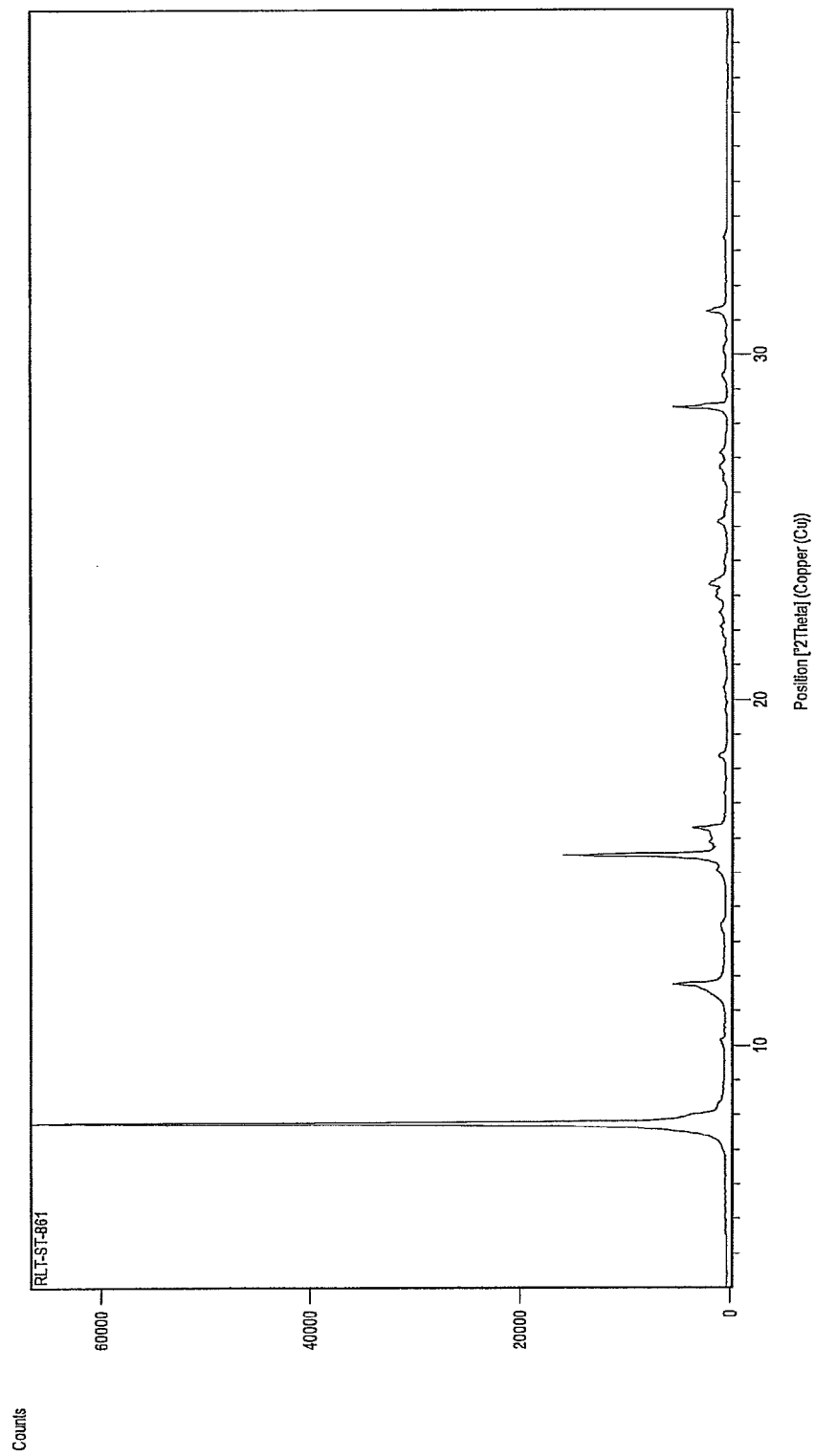
Figure 25: A characteristic X-ray powder diffractogram of Raltegravir free hydroxy Form A3

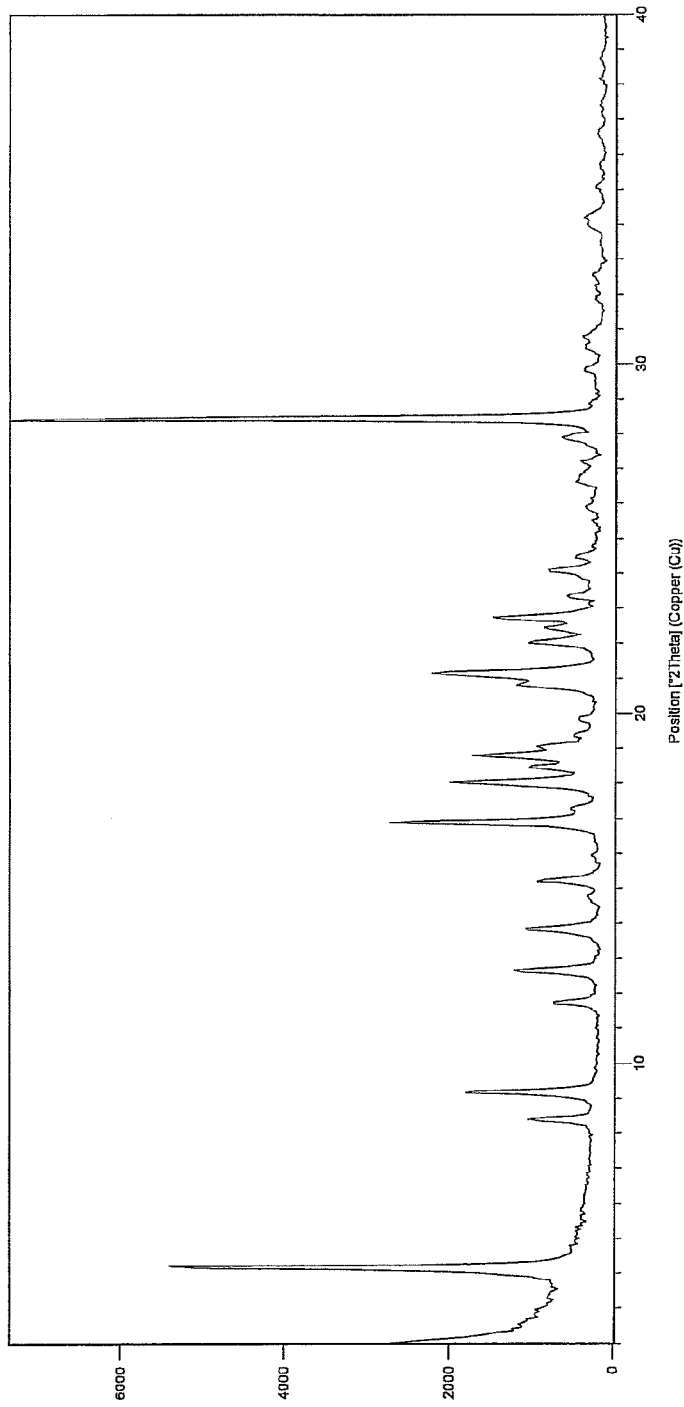
Figure 26: A characteristic X-ray powder diffractogram of Raltegravir *tert*-butylamine salt.
* The peak at 28.4 corresponds to silicon powder (Si).

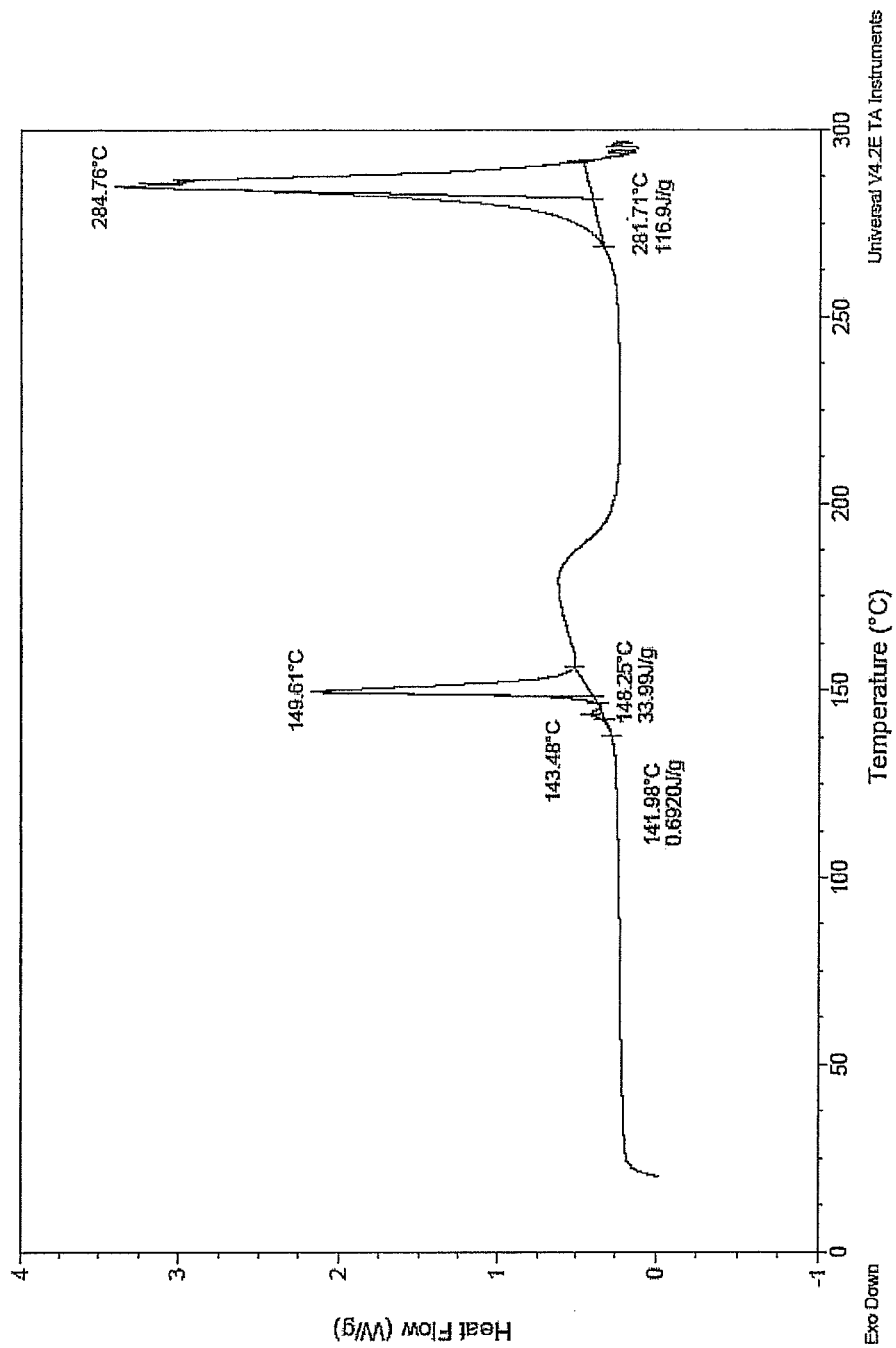
Figure 27: A DSC thermogram for Raltegravir potassium Form IV.

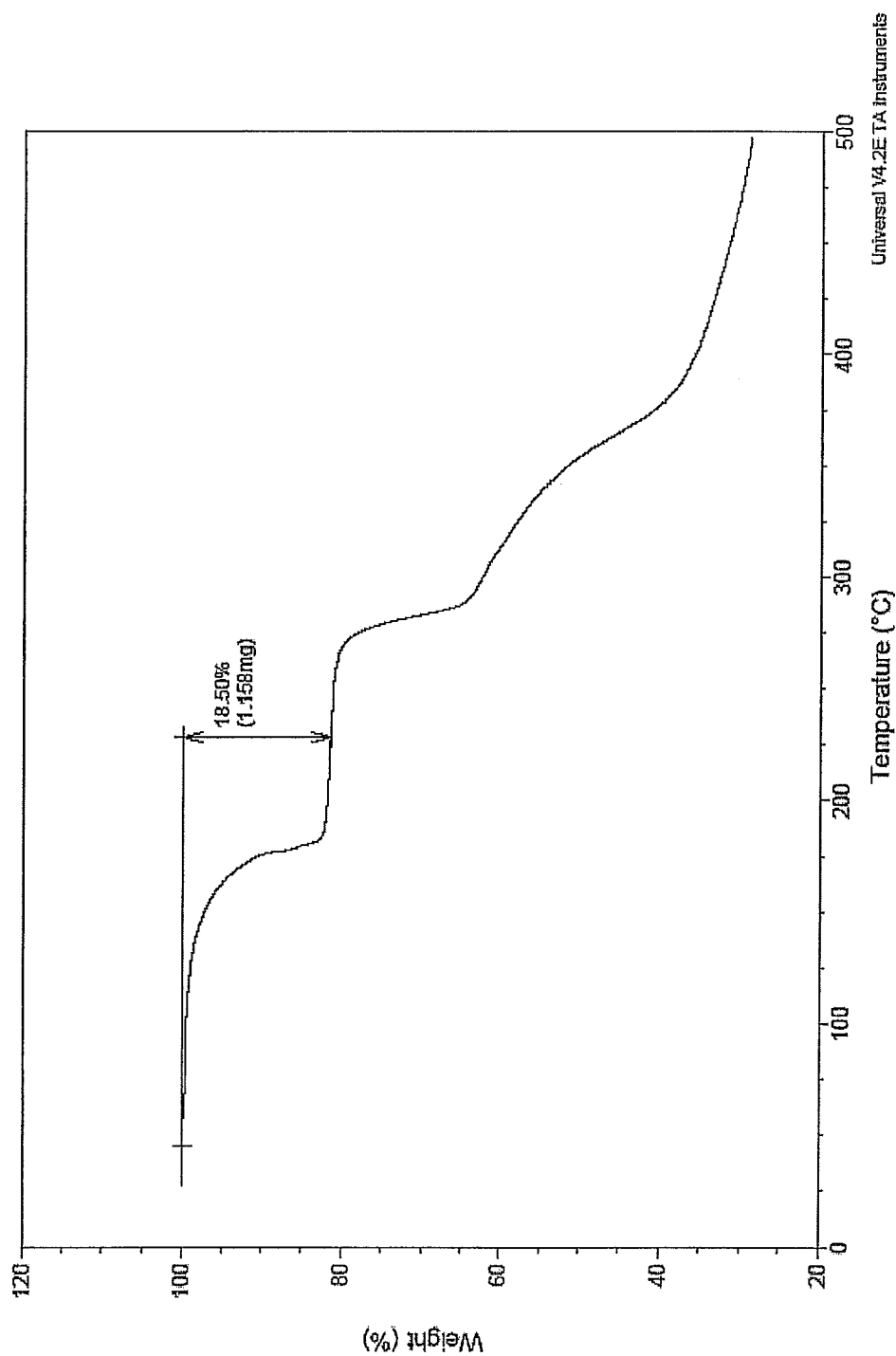
Figure 28: A TGA thermogram of Raltegravir potassium Form IV.

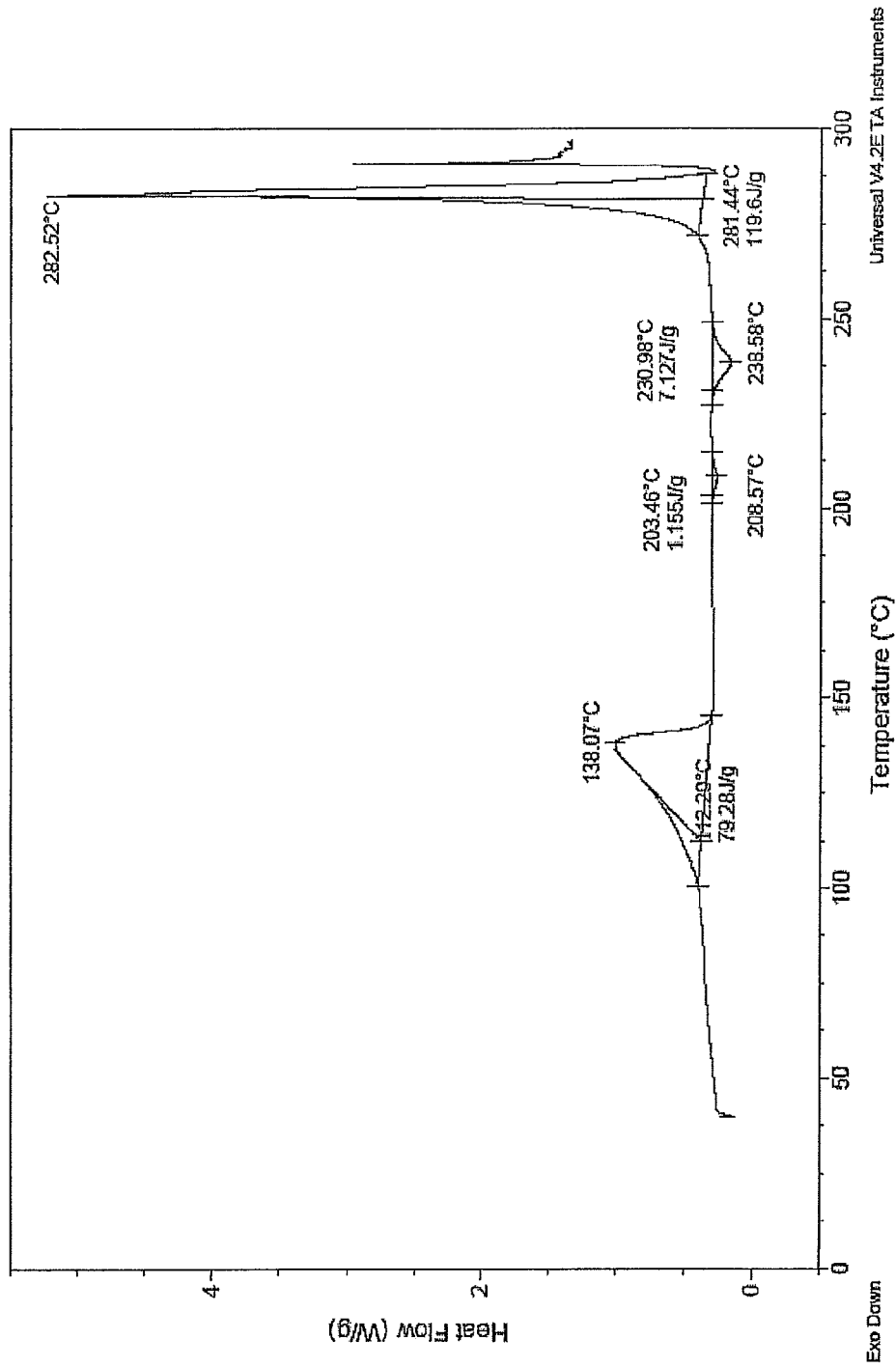
Figure 29: A DSC thermogram for Raltegravir potassium Form V.

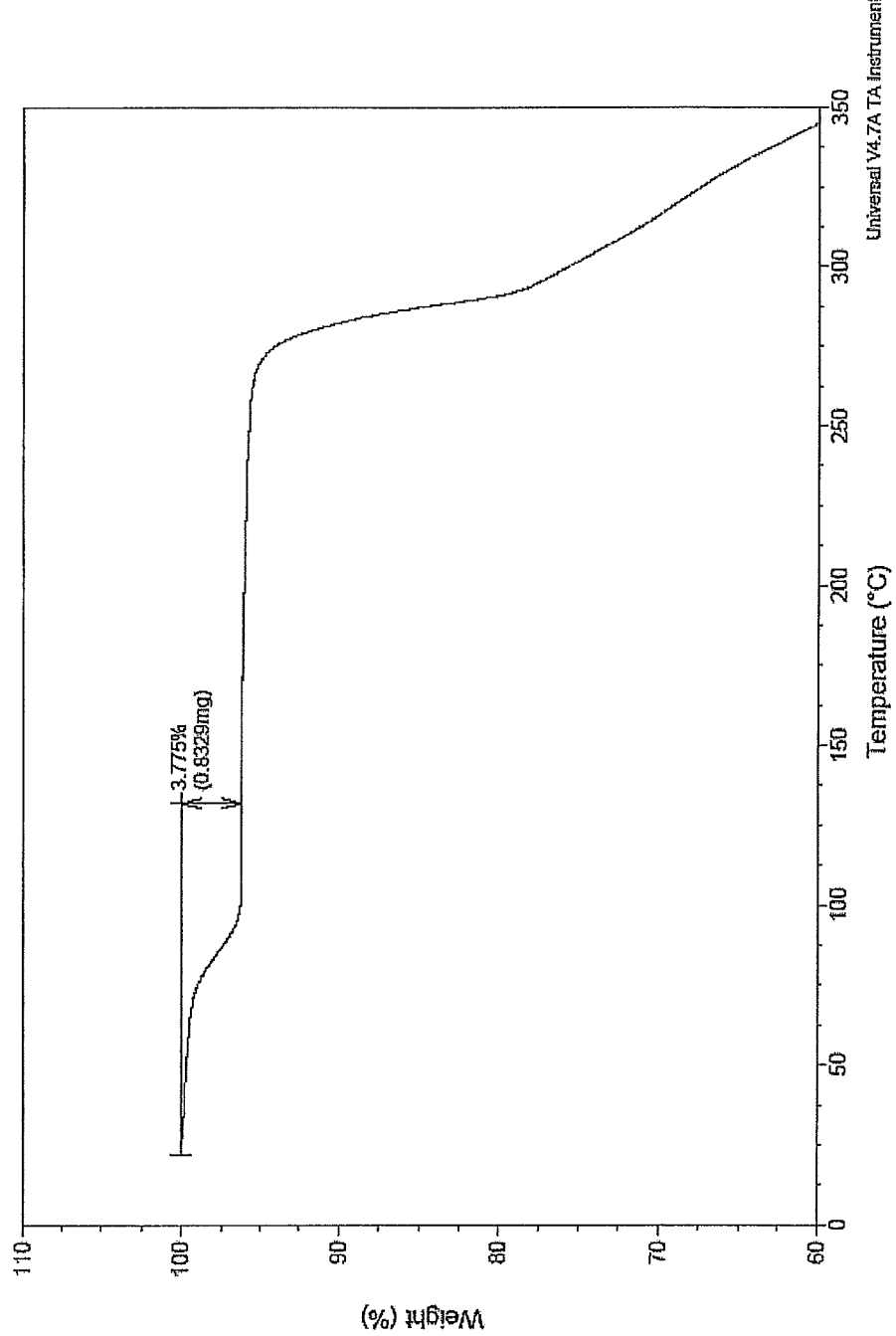
Figure 30: A TGA thermogram of Raltegravir potassium Form V.

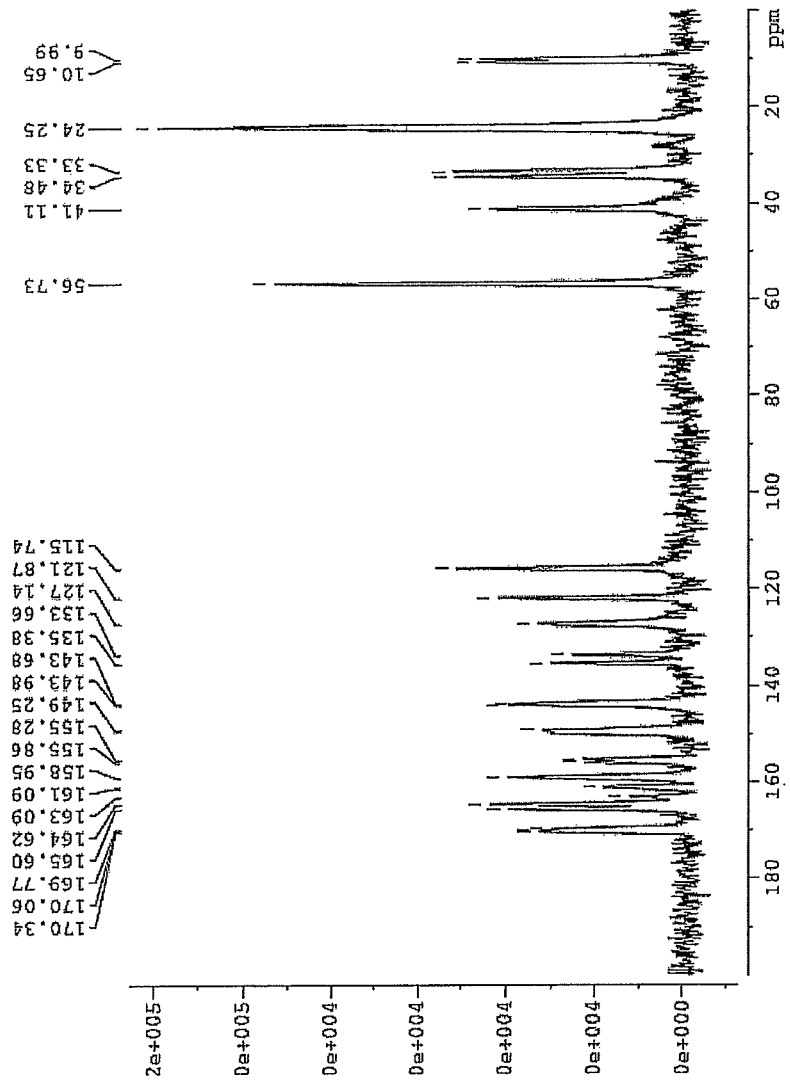
Figure 31: a solid-state $^{13}$C NMR spectrum of Raltegravir potassium Form V.

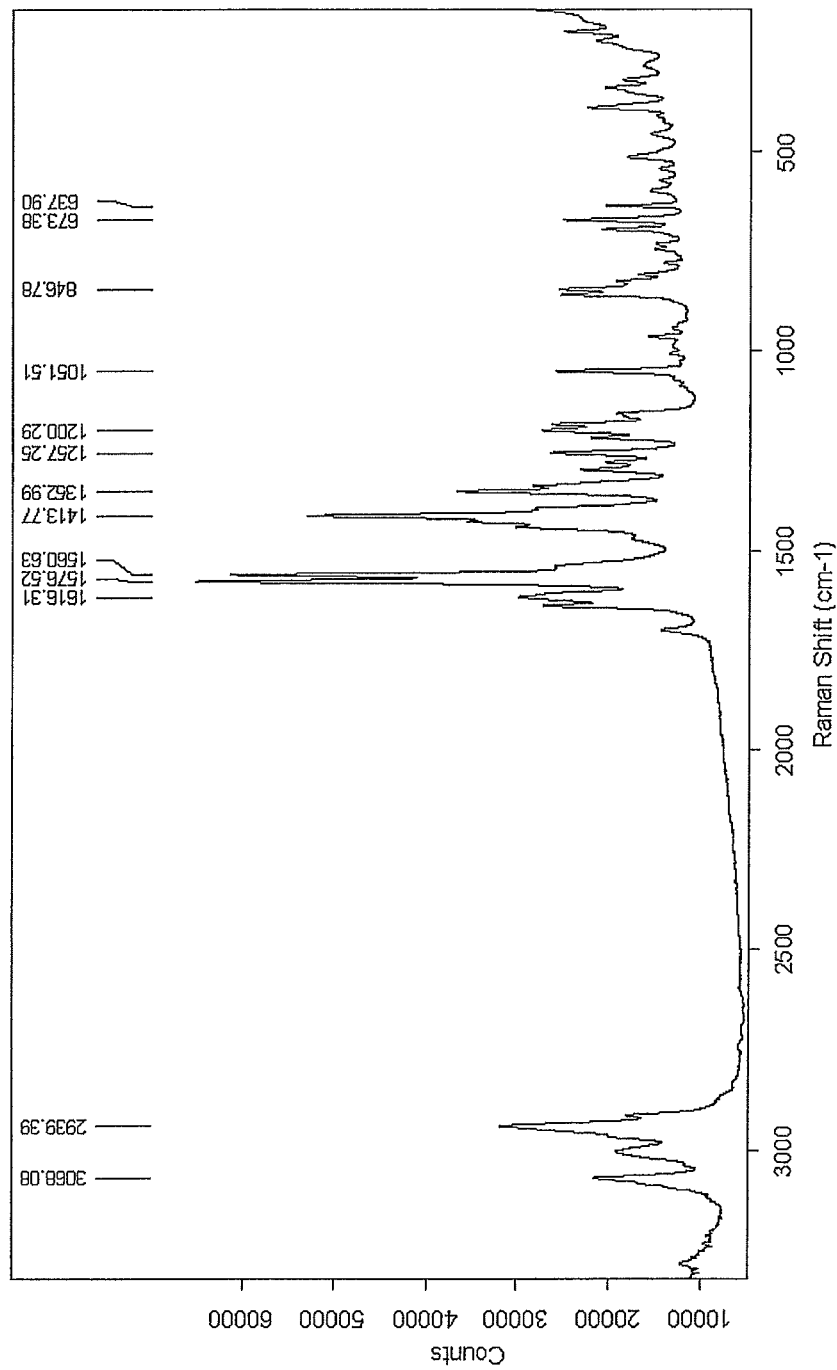
Figure 32: an FT Raman spectrum of Raltegravir potassium Form V (monohydrate).

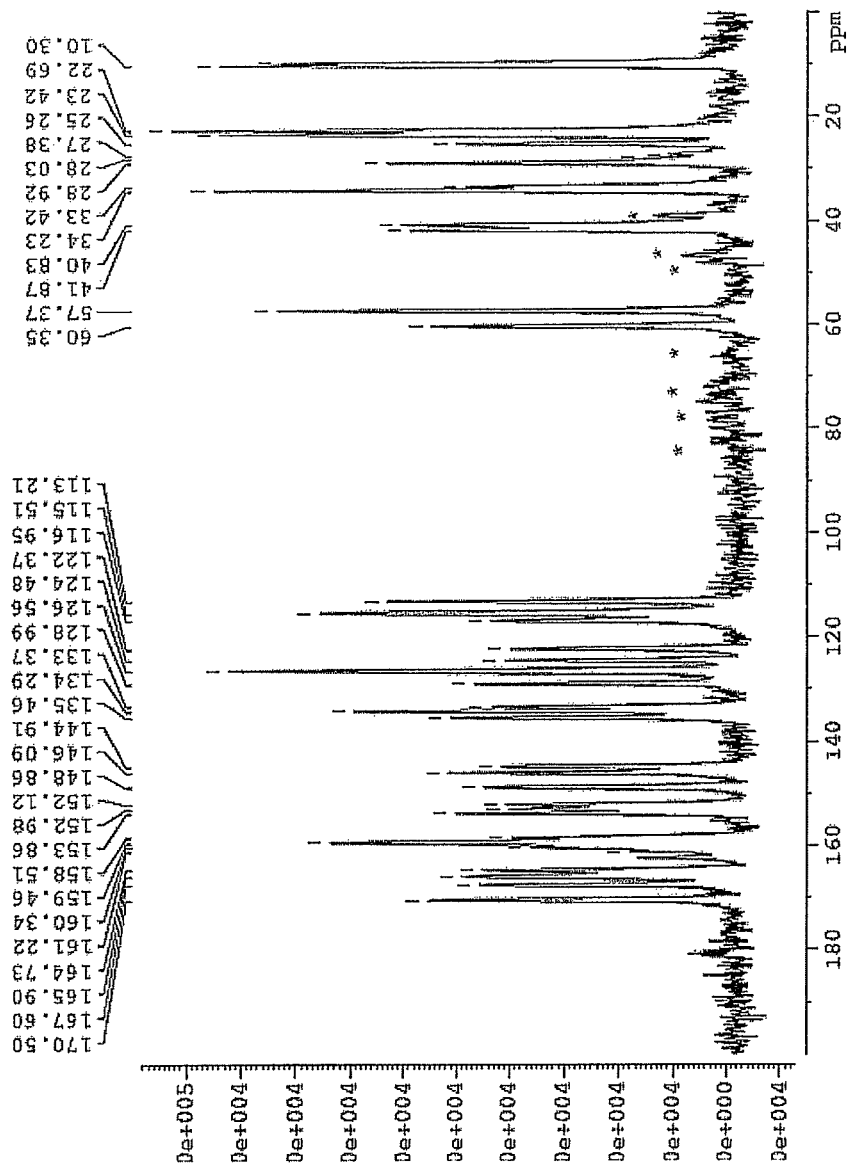
Figure 33: a solid-state $^{13}$C NMR spectrum of Raltegravir sodium Form S2.

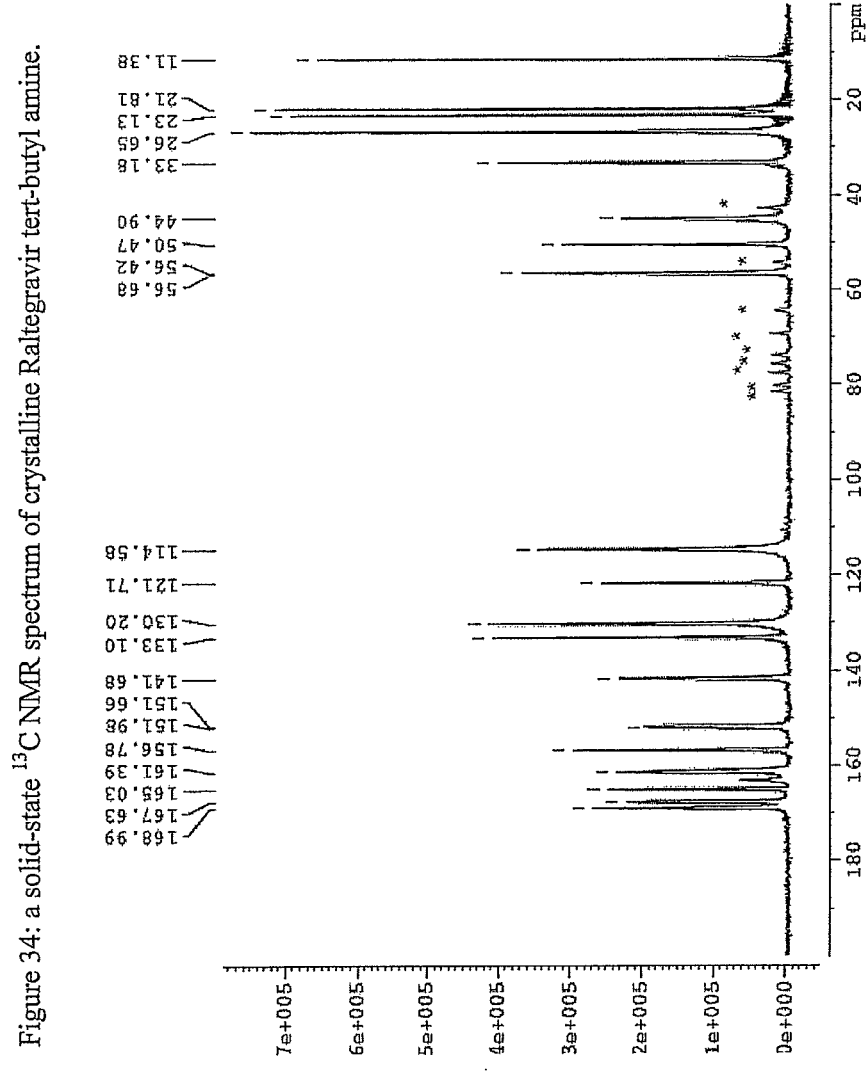
Figure 34: a solid-state ¹³C NMR spectrum of crystalline Raltegravir tert-butyl amine.

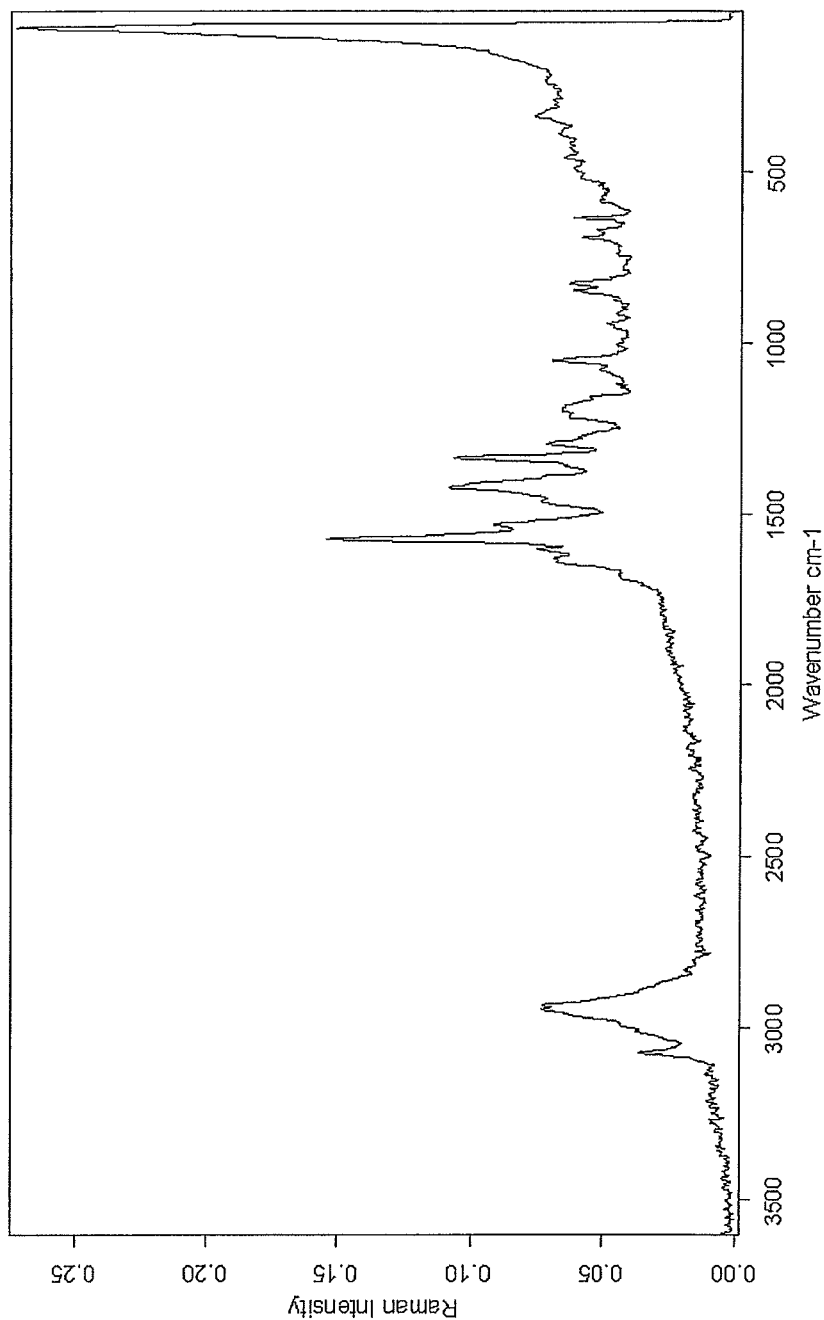
Figure 35: an FT Raman spectrum of Raltegravir meglumine salt.

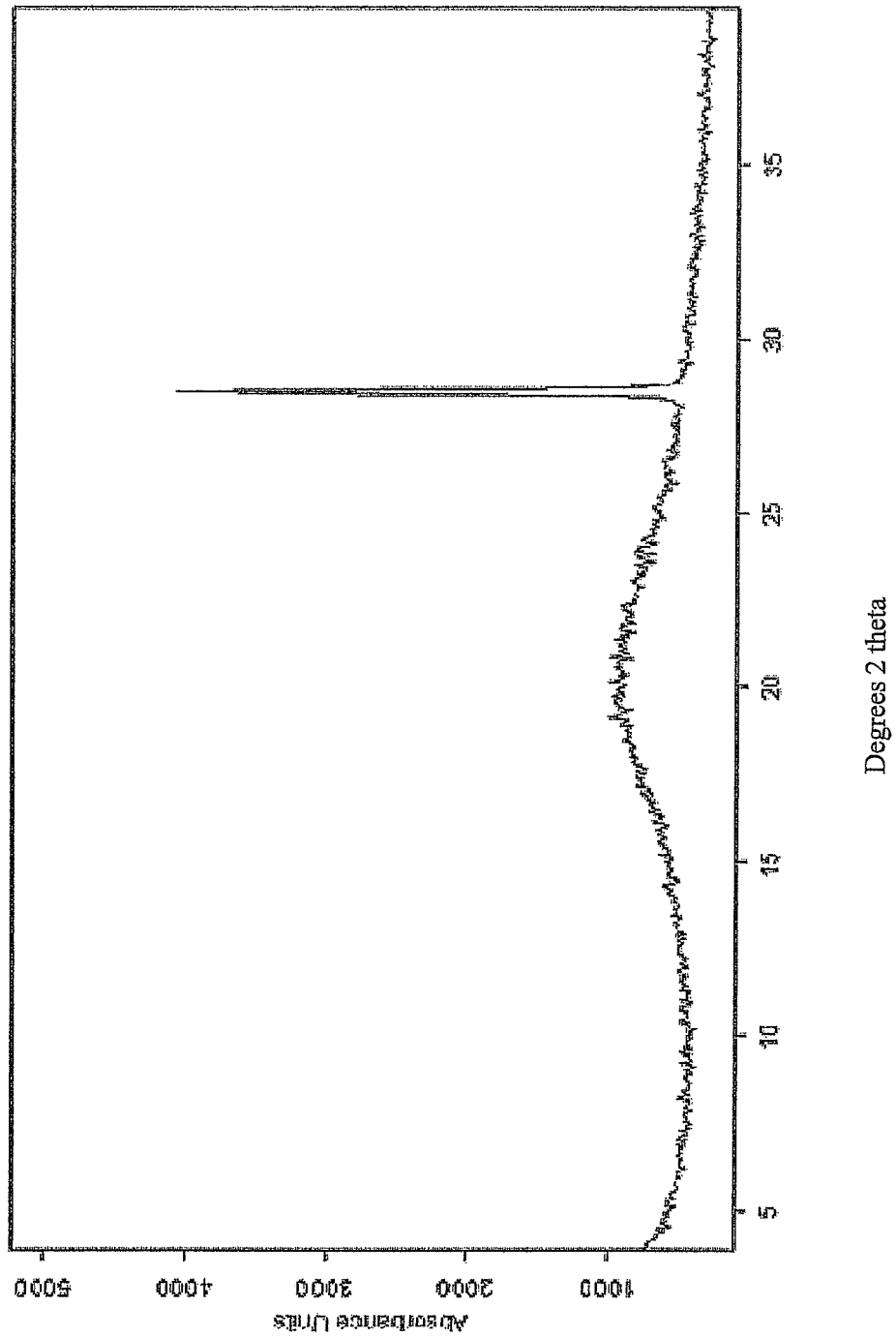
Figure 36: A characteristic X-ray powder diffractogram of amorphous Raltegravir meglumine salt.

RALTEGRAVIR SALTS AND CRYSTALLINE FORMS THEREOF

This application claims the priority of U.S. Provisional Patent Application Nos. 61/320,062 filed Apr. 1, 2010; 61/326,922 filed Apr. 22, 2010; 61/329,284 filed Apr. 29, 2010; 61/353,398 filed Jun. 10, 2010; 61/392,759 filed Oct. 13, 2010; 61/392,770 filed Oct. 13, 2010; and 61/417,632 filed Nov. 29, 2010, the disclosures of which applications are incorporated by reference.

FIELD OF THE INVENTION

The present invention encompasses Raltegravir salts and their solid state forms, as well as crystalline forms of Raltegravir potassium and sodium salts and of Raltegravir free hydroxy.

BACKGROUND OF THE INVENTION

Raltegravir, also referred to as Raltegravir free hydroxy, N-(2-(4-(4-fluorobenzylcarbamoyl)-5-hydroxy-1-methyl-6-oxo-1,6-dihydropyrimidin-2-yl)propan-2-yl)-5-methyl-1,3,4-oxadiazole-2-carboxamide, having the following formula;

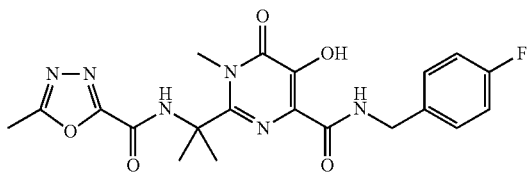 [SMILES: Cc1nnc(C(=O)NC(C)(C)c2nc(C(=O)NCc3ccc(F)cc3)c(O)c(=O)n2C)o1]

is an antiretroviral drug used to treat HIV infection. Raltegravir targets integrase, an HIV enzyme that integrates the viral genetic material into human chromosomes, a critical step in the pathogenesis of HIV. Raltegravir potassium salt is marketed under the trade name ISENTRESS™ by Merck & Co.

Raltegravir and its preparation are described in U.S. Pat. No. 7,169,780. US Publication No. US 2006/0122205, WO 2010/140156 and WO 2011/024192 describe potassium salt of Raltegravir including amorphous and crystalline forms I, II, III and H1 as well as amorphous and crystalline forms of Raltegravir free-hydroxy.

The present invention relates to salts of Raltegravir, as well as solid state forms of Raltegravir and Raltegravir salts. These properties can be influenced by controlling the conditions under which Raltegravir potassium, Raltegravir sodium, Raltegravir calcium, Raltegravir tert-butyl amine, Raltegravir lithium, Raltegravir diethylamine, Raltegravir diisopropylamine, Raltegravir meglumine and Raltegravir free hydroxy, are obtained in solid form.

Polymorphism, the occurrence of different crystal forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray diffraction pattern, infrared absorption fingerprint, and solid state NMR spectrum. One or more of these techniques may be used to distinguish different polymorphic forms of a compound.

Discovering new salts and new polymorphic forms and solvates of a pharmaceutical product can provide materials having desirable processing properties, such as ease of handling, ease of processing, storage stability, ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. For at least these reasons, there is a need for additional salts and solid state forms of Raltegravir potassium, sodium, calcium, tert-butyl amine, meglumine, lithium, diethylamine and diisopropylamine salts and of Raltegravir free-hydroxy.

SUMMARY OF THE INVENTION

The present invention provides salts of Raltegravir and crystalline forms thereof and of Raltegravir free hydroxy, processes for preparing them, and pharmaceutical composition containing them.

The present invention also encompasses the use of any one of the Raltegravir salts, Raltegravir free-hydroxy and crystalline forms thereof of the present invention for the preparation of Raltegravir potassium or formulation thereof, for use as medicaments, particularly for the treatment of HIV infection.

The present invention also provides a process for preparing Raltegravir potassium, by preparing any one of the Raltegravir salts and crystalline forms thereof or of Raltegravir free-hydroxy, and converting it to Raltegravir potassium.

The present invention further provides a pharmaceutical composition comprising any one of the Raltegravir salts, Raltegravir free-hydroxy and crystalline forms thereof of the present invention and at least one pharmaceutically acceptable excipient, for use as medicaments, particularly for the treatment of HIV infection.

The present invention also provides a method of treating HIV infection, comprising administering a therapeutically effective amount of at least one of the Raltegravir salts, Raltegravir free-hydroxy and crystalline forms thereof of the present invention, or at least one of the above pharmaceutical compositions to a person suffering from an HIV

BRIEF DESCRIPTION OF THE DRAWINGS

FIG. 1 shows an X-ray powder diffractogram of Raltegravir potassium Form IV.

FIG. 2 shows an X-ray powder diffractogram of Raltegravir potassium Form V.

FIG. 3 shows an X-ray powder diffractogram of Raltegravir potassium Form VI.

FIG. 4 shows an X-ray powder diffractogram of Raltegravir potassium Form VII.

FIG. 5 shows an X-ray powder diffractogram of Raltegravir potassium Form VIII.

FIG. 6 shows an X-ray powder diffractogram of Raltegravir potassium Form IXa.

FIG. 7 shows an X-ray powder diffractogram of Raltegravir potassium Form IXb.

FIG. 8 shows an X-ray powder diffractogram of Raltegravir potassium Form X, with the values in the horizontal axis expressed in degrees 2θ.

FIG. 9 shows an X-ray powder diffractogram of Raltegravir potassium Form XI.

FIG. 10 shows an X-ray powder diffractogram of Raltegravir potassium Form XII.

FIG. 11 shows an X-ray powder diffractogram of Raltegravir potassium Form XIII.

FIG. 12 shows an X-ray powder diffractogram of Raltegravir sodium Form S1.

FIG. 13 shows an X-ray powder diffractogram of Raltegravir sodium Form S2.

FIG. 14 shows an X-ray powder diffractogram of Raltegravir sodium Form S3.

FIG. 15 shows an X-ray powder diffractogram of Raltegravir lithium salt.

FIG. 16 shows an X-ray powder diffractogram of Raltegravir calcium salt

FIG. 17 shows an X-ray powder diffractogram of Raltegravir tert-butyl amine salt.

FIG. 18 shows an X-ray powder diffractogram of Raltegravir diethylamine salt

FIG. 19 shows an X-ray powder diffractogram of Raltegravir diisopropylamine salt FIG. 20 shows an X-ray powder diffractogram of Raltegravir potassium Form XIV.

FIG. 21 shows an X-ray powder diffractogram of Raltegravir potassium Form XV

FIG. 22 shows an X-ray powder diffractogram of Raltegravir potassium Form XVI.

FIG. 23 shows an X-ray powder diffractogram of Raltegravir free hydroxy Form A1.

FIG. 24 shows an X-ray powder diffractogram of Raltegravir free hydroxy Form A2.

FIG. 25 shows an X-ray powder diffractogram of Raltegravir free hydroxy Form A3.

FIG. 26 shows an X-ray powder diffractogram of Raltegravir tert-butyl amine salt.

FIG. 27 shows a DSC thermogram for Raltegravir potassium form IV.

FIG. 28 shows a TGA thermogram of Raltegravir potassium form IV.

FIG. 29 shows a DSC thermogram for Raltegravir potassium form V.

FIG. 30 shows a TGA thermogram of Raltegravir potassium form V.

FIG. 31 shows a solid-state $^{13}C$ NMR spectrum of Raltegravir potassium form V.

FIG. 32 shows an FT Raman spectrum of Raltegravir potassium form V.

FIG. 33 shows a solid-state $^{13}C$ NMR spectrum of Raltegravir sodium form S2.

FIG. 34 shows a solid-state $^{13}C$ NMR spectrum of crystalline Raltegravir tert-butyl amine.

FIG. 35 shows an FT Raman spectrum of Raltegravir meglumine salt.

FIG. 36 shows an X-ray powder diffractogram of amorphous Raltegravir meglumine salt.

DETAILED DESCRIPTION OF THE INVENTION

The present invention encompasses the following new salts and solid state forms of Raltegravir: Raltegravir calcium salt (N-(2-(4-(4-fluorobenzylcarbamoyl)-5-hydroxy-1-methyl-6-oxo-1,6-dihydropyrimidin-2-yl)propan-2-yl)-5-methyl-1,3,4-oxadiazole-2-carboxamide calcium salt); Raltegravir tert-butyl amine salt (N-(2-(4-(4-fluorobenzyl-carbamoyl)-5-hydroxy-1-methyl-6-oxo-1,6-dihydropyrimidin-2-yl)propan-2-yl)-5-methyl-1,3,4-oxadiazole-2-carboxamide tert-butyl amine salt); Raltegravir meglumine salt (N-(2-(4-(4-fluorobenzylcarbamoyl)-5-hydroxy-1-methyl-6-oxo-1,6-dihydropyrimidin-2-yl)propan-2-yl)-5-methyl-1,3,4-oxadiazole-2-carboxamide meglumine salt); Raltegravir lithium salt (N-(2-(4-(4-fluorobenzylcarbamoyl)-5-hydroxy-1-methyl-6-oxo-1,6-dihydropyrimidin-2-yl)propan-2-yl)-5-methyl-1,3,4-oxadiazole-2-carboxamide lithium salt); Raltegravir diethylamine salt (N-(2-(4-(4-fluorobenzylcarbamoyl)-5-hydroxy-1-methyl-6-oxo-1,6-dihydropyrimidin-2-yl)propan-2-yl)-5-methyl-1,3,4-oxadiazole-2-carboxamide diethylamine salt); and Raltegravir diisopropylamine salt (N-(2-(4-(4-fluorobenzylcarbamoyl)-5-hydroxy-1-methyl-6-oxo-1,6-dihydropyrimidin-2-yl)propan-2-yl)-5-methyl-1,3,4-oxadiazole-2-carboxamide diisopropylamine salt).

The present invention also encompasses crystalline forms of Raltegravir potassium salt (N-(2-(4-(4-fluorobenzylcarbamoyl)-5-hydroxy-1-methyl-6-oxo-1,6-dihydropyrimidin-2-yl)propan-2-yl)-5-methyl-1,3,4-oxadiazole-2-carboxamide potassium salt); Raltegravir sodium salt (N-(2-(4-(4-fluorobenzylcarbamoyl)-5-hydroxy-1-methyl-6-oxo-1,6-dihydropyrimidin-2-yl)propan-2-yl)-5-methyl-1,3,4-oxadiazole-2-carboxamide sodium salt); and Raltegravir free-hydroxy (N-(2-(4-(4-fluorobenzylcarbamoyl)-5-hydroxy-1-methyl-6-oxo-1,6-dihydropyrimidin-2-yl)propan-2-yl)-5-methyl-1,3,4-oxadiazole-2-carboxamide).

In some embodiments, salts and solid state forms of Raltegravir of the invention are substantially free of any other salts, polymorphic forms, or of specified polymorphic forms of Raltegravir, respectively. In any embodiment of the present invention, by "substantially free" is meant that the forms of the present invention contain 20% (w/w) or less, 10% (w/w) or less, 5% (w/w) or less, 2% (w/w) or less, particularly 1% (w/w) or less, more particularly 0.5% (w/w) or less, and most particularly 0.2% (w/w) or less of any other salts, polymorphs or of a specified polymorph of Raltegravir. In other embodiments, the salts and polymorphs of Raltegravir potassium, sodium, calcium, tert-butyl amine, meglumine, lithium, diethylamine or diisopropylamine salts and of Raltegravir free-hydroxy of the invention contain from 1% to 20% (w/w), from 5% to 20% (w/w), or from 5% to 10% (w/w) of any other salts, polymorphs or of a specified polymorph of Raltegravir.

The present invention addresses a need in the art by providing new crystalline forms of Raltegravir potassium, Raltegravir sodium, Raltegravir free-hydroxy and other Raltegravir salts (particularly, lithium, calcium, tert-butylamine, meglumine, diethylamine or diisopropylamine salts) that have advantageous properties selected from at least one of: chemical purity, flowability, solubility, dissolution rate, morphology or crystal habit, stability—such as thermal and mechanical stability to polymorphic conversion, stability to dehydration and/or storage stability, low content of residual solvent, a lower degree of hygroscopicity, flowability, and advantageous processing and handling characteristics such as compressibility, and bulk density.

A crystal form may be referred to herein as being characterized by graphical data "as depicted in" a Figure. Such data include, for example, powder X-ray diffractograms and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of a Raltegravir salt referred to herein as being characterized by graphical data "as depicted in" a Figure will thus be understood to include any crystal forms of the Raltegravir salt characterized with the graphical data having such small variations, as are well known to the skilled person, in comparison with the Figure.

As used herein, the term "monohydrate" refers to hydrate containing water in crystal lattice, in equimolar amount compared to the compound. In particularly, the compound is Raltegravir potassium.

As used herein, the term "solvate" refers to a crystal lattice containing solvent. Particularly, the crystal lattice is of Raltegravir potassium and the solvent is NMP.

As used herein, the term "isolated" in reference to any of Raltegravir salts or polymorphs thereof of the present invention corresponds to Raltegravir salt or polymorph thereof that is physically separated from the reaction mixture, where it is formed.

As used herein, unless stated otherwise, the XRPD measurements are taken using copper Kα radiation wavelength 1.54 Å.

A thing, e.g., a reaction mixture, may be characterized herein as being at, or allowed to come to "room temperature, often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure of about 10 mbar to about 50 mbar.

As used herein, the terms "vol." or "volume" can be used to refer to nil per gram of the corresponding raltegravir. For example, a statement that 0.5 g of Raltegravir is dissolved in ten volumes of a Solvent X would be understood to mean that the 0.5 g of Raltegravir was dissolved in 5 ml of Solvent X.

The present invention encompasses a crystalline form of Raltegravir potassium, designated as Form IV. Form IV can be characterized by data selected from: an X-ray powder diffraction pattern having peaks at 6.5, 7.5, 8.1, 18.4 and 23.2 degrees two theta ±0.2 degrees two theta; an X-ray powder diffraction pattern substantially as depicted in FIG. 1; and combinations thereof. Crystalline Form IV of Raltegravir potassium may be further characterized by the X-ray powder diffraction pattern having additional peaks at 13.0, 17.5, 24.2 and 25.5 degrees two theta ±0.2 degrees two theta; a DSC thermogram as depicted in FIG. 27; a TGA thermogram as depicted in FIG. 28; and combinations thereof.

Typically, Raltegravir potassium Form IV can be an N-methyl-pyrrolidone ("NMP") solvate.

The present invention encompasses a crystalline form of Raltegravir potassium, designated as Form V. Form V can be characterized by data selected from: an X-ray powder diffraction pattern having peaks at 8.0, 11.9, 18.2 and 26.6 degrees two theta ±0.2 degrees two theta; an X-ray powder diffraction pattern substantially as depicted in FIG. 2; a solid-state $^{13}C$ NMR spectrum with signals at 121.9, 144.0, 149.3 and 170.3±0.2 ppm; a solid-state $^{13}C$ NMR spectrum having chemical shifts differences between the signal exhibiting the lowest chemical shift and another in the chemical shift range of 100 to 180 ppm of 111.9, 134.0, 139.3 and 160.3±0.1 ppm; a solid-state $^{13}C$ NMR spectrum substantially as depicted in FIG. 31; and combinations thereof. Crystalline Form V of Raltegravir potassium may be further characterized by the X-ray powder diffraction pattern having additional peaks at 14.9, 19.8, 24.9, 27.7 and 28.9 degrees two theta ±0.2 degrees two theta; a DSC thermogram as depicted in FIG. 29; a TGA thermogram as depicted in FIG. 30; an FT Raman spectrum as depicted in FIG. 32; and combinations thereof.

Typically, Raltegravir potassium Form V can be a monohydrate, for example, it can contain from about 3.4% to about 3.8% of water, specifically, about 3.6% of water by weight.

As discussed above, Raltegravir potassium Form V has advantageous properties. In particular, the crystalline Raltegravir potassium Form V of the present invention has a significantly higher dissolution rate compared with the Raltegravir potassium Form I disclosed in U.S. Pat. No. 7,754,731, which lead to favourable pharmacokinetics, e.g. increased bioavailability of Raltegravir.

Raltegravir potassium Form V of the present invention may be prepared by a process comprising: combining Raltegravir free-hydroxy with tetrahydrofuran ("THF") to obtain a reaction mixture; and adding an aqueous solution of KOH. Typically, the Raltegravir free hydroxy is Raltegravir free hydroxy Form A1. The addition of the aqueous solution of KOH may be followed by a cooling step. The cooling may be done to a temperature such as about −10° C. to about 5° C., or about 0° C. The cooling may be followed by seeding with Raltegravir potassium Form V. Following the cooling, the reaction mixture may be maintained, typically while stirring. The maintaining may be done for a time period such as about 2.5 hours to about 48 hours, for example, for about 2.5 hours. The obtained Raltegravir potassium may further be isolated. The isolation may be done by filtering and washing with a suitable solvent, preferably a water miscible solvent such as THF. Typically, the filtering is done at room temperature. Optionally, the isolated precipitate is further dried.

The present invention further encompasses a crystalline form of Raltegravir potassium, designated as Form VI. Form VI can be characterized by data selected from: an X-ray powder diffraction pattern having peaks at 5.7, 12.7, 17.1, 19.7 and 25.4 degrees two theta ±0.2 degrees two theta; an X-ray powder diffraction pattern substantially as depicted in FIG. 3; and combinations thereof. Crystalline Form VI of Raltegravir potassium may be further characterized by the X-ray powder diffraction pattern having additional peaks at 11.4, 15.8 and 20.3 degrees two theta ±0.2 degrees two theta.

The present invention encompasses a crystalline form of Raltegravir potassium, designated as Form VII. Form VII can be characterized by data selected from: an X-ray powder diffraction pattern having peaks at 7.4, 11.1, 16.0 and 25.8 degrees two theta ±0.2 degrees two theta; an X-ray powder diffraction pattern substantially as depicted in FIG. 4; and combinations thereof. Crystalline Form VII of Raltegravir potassium may be further characterized by the X-ray powder diffraction pattern having additional peaks at 22.4, 25.2, 26.7 and 28.7 degrees two theta ±0.2 degrees two theta.

The present invention encompasses a crystalline form of Raltegravir potassium, designated as Form VIII. Form VIII can be characterized by data selected from: an X-ray powder diffraction pattern having peaks at 5.4, 7.4, 13.1, 13.4, 20.6, 22.3, 24.6 and 26.4 degrees two theta ±0.2 degrees two theta; an X-ray powder diffraction pattern substantially as depicted in FIG. 5; and combinations thereof. Crystalline Form VIII of Raltegravir potassium may be further characterized by the X-ray powder diffraction pattern having additional peaks at 14.6, 20.1, 23.0, 24.1, 27.9, 28.9 and 29.5 degrees two theta ±0.2 degrees two theta.

The present invention encompasses a crystalline form of Raltegravir potassium, designated as Form IXa. Form IXa can be characterized by data selected from: an X-ray powder diffraction pattern having peaks at 5.3, 7.2, 8.2, 10.6 and 13.7 degrees two theta ±0.2 degrees two theta; an X-ray powder diffraction pattern substantially as depicted in FIG. 6; and combinations thereof. Crystalline Form IXa of Raltegravir potassium may be further characterized by the X-ray powder diffraction pattern having additional peaks at 16.0, 17.2, 18.6, 21.4 and 24.3 degrees two theta ±0.2 degrees two theta.

The present invention encompasses a crystalline form of Raltegravir potassium, designated as Form IXb. Form IXb can be characterized by data selected from: an X-ray powder diffraction pattern having peaks at 5.3, 7.8, 8.2, 10.6, 12.2 and 13.7 degrees two theta ±0.2 degrees two theta; an X-ray powder diffraction pattern substantially as depicted in FIG. 7; and combinations thereof. Crystalline Form IXb of Raltegravir potassium may be further characterized by the X-ray powder diffraction pattern having additional peaks at 18.9, 19.8, 20.1, 21.5, 22.2 and 24.3 degrees two theta ±0.2 degrees two theta.

The present invention encompasses a crystalline form of Raltegravir potassium, designated as Form X. Form X can be characterized by data selected from: an X-ray powder diffraction pattern having peaks at 5.7, 8.3, 15.4, 19.1, 19.8 and 20.3 degrees two theta ±0.2 degrees two theta; an X-ray powder diffraction pattern substantially as depicted in FIG. 8; and combinations thereof. Crystalline Form X of Raltegravir potassium may be further characterized by the X-ray powder diffraction pattern having additional peaks at 22.5, 24.5, 25.4 and 26.8 degrees two theta ±0.2 degrees two theta.

The present invention encompasses a crystalline form of Raltegravir potassium, designated as Form XI. Form XI can be characterized by data selected from: an X-ray powder diffraction pattern having peaks at 7.9, 14.5, 15.8, 17.3, 21.1 and 23.0 degrees two theta ±0.2 degrees two theta; an X-ray powder diffraction pattern substantially as depicted in FIG. 9; and combinations thereof.

The present invention comprises a crystalline foul of Raltegravir potassium, designated as Form XII. Form XII can be characterized by data selected from: an X-ray powder diffraction pattern having peaks at 5.2; 8.3; 15.5; 19.1; and 28.5 degrees two theta ±0.2 degrees two theta; an X-ray powder diffraction pattern substantially as depicted in FIG. 10; and combinations thereof. Crystalline Form XII of Raltegravir potassium may be further characterized by the X-ray powder diffraction pattern having additional peaks at 7.0; 7.5; 11.8; 12.3; 14.7; and 18.1 degrees two theta ±0.2 degrees two theta.

The present invention comprises a crystalline form of Raltegravir potassium, designated as Form XIII. Form XIII can be characterized by data selected from: an X-ray powder diffraction pattern having peaks at 5.1; 7.2; 7.7; 7.9; 11.9; and 24.3 degrees two theta ±0.2 degrees two theta; an X-ray powder diffraction pattern substantially as depicted in FIG. 11; and combinations thereof.

The present invention comprises a crystalline form of Raltegravir potassium, designated as Form XIV. Form XIV can be characterized by data selected from: an X-ray powder diffraction pattern having peaks at 4.9, 7.7, 19.4, 24.1 and 25.9 degrees two theta ±0.2 degrees two theta; an X-ray powder diffraction pattern substantially as depicted in FIG. 20; and combinations thereof. Crystalline Form XIV of Raltegravir potassium may be further characterized by the X-ray powder diffraction pattern having additional peaks at 13.4, 13.8, 21.3, 24.5 and 30.8 degrees two theta ±0.2 degrees two theta.

The present invention comprises a crystalline form of Raltegravir potassium, designated as Form XV. Form XV can be characterized by data selected from: an X-ray powder diffraction pattern having peaks at 5.2, 11.5, 15.6 and 23.1 degrees two theta ±0.2 degrees two theta; an X-ray powder diffraction pattern substantially as depicted in FIG. 21; and combinations thereof. Crystalline Form XV of Raltegravir potassium may be further characterized by the X-ray powder diffraction pattern having additional peaks at 11.9, 12.9, 18.6 and 25.5 degrees two theta ±0.2 degrees two theta.

The present invention comprises a crystalline form of Raltegravir potassium, designated as Form XVI. Form XVI can be characterized by data selected from: an X-ray powder diffraction pattern having peaks at 4.6, 9.3, 13.9, 18.2 and 18.6 degrees two theta ±0.2 degrees two theta; an X-ray powder diffraction pattern substantially as depicted in FIG. 22; and combinations thereof. Crystalline Form XVI of Raltegravir potassium may be further characterized by the X-ray powder diffraction pattern having additional peaks at 13.4, 15.0, 22.1, and 23.6 degrees two theta ±0.2 degrees two theta.

The present invention encompasses isolated Raltegravir sodium salt. Typically, the Raltegravir sodium salt can be in a crystalline form.

The present invention encompasses a crystalline form of Raltegravir sodium, designated as Form S1. Form S1 can be characterized by data selected from: an X-ray powder diffraction pattern having peaks at 7.9, 11.8, 17.0, 19.7 and 28.8 degrees two theta ±0.2 degrees two theta; an X-ray powder diffraction pattern substantially as depicted in FIG. 12; and combinations thereof. Crystalline Form S1 of Raltegravir sodium may be further characterized by the X-ray powder diffraction pattern having additional peaks at 14.0, 15.0, 23.9 and 27.8 degrees two theta ±0.2 degrees two theta.

The present invention encompasses a crystalline form of Raltegravir sodium, designated as Fowl S2. Form S2 can be characterized by data selected from: an X-ray powder diffraction pattern having peaks at 7.8, 11.8, 19.6 and 26.3 degrees two theta ±0.2 degrees two theta; an X-ray powder diffraction pattern substantially as depicted in FIG. 13; a solid-state $^{13}$C NMR spectrum with signals at 134.3, 146.1, 149.0, 153.9 and 170.5±0.2 ppm; a solid-state $^{13}$C NMR spectrum having chemical shifts differences between the signal exhibiting the lowest chemical shift and another in the chemical shift range of 100 to 180 ppm of 124.3, 136.1, 139.0, 143.9 and 160.5±0.1 ppm; a solid-state $^{13}$C NMR spectrum substantially as depicted in FIG. 33; and combinations thereof. Crystalline Form S2 of Raltegravir sodium may be further characterized by the X-ray powder diffraction pattern having additional peaks at 14.6, 17.2, 23.6, 28.1 and 29.1 degrees two theta ±0.2 degrees two theta.

The present invention encompasses a crystalline form of Raltegravir sodium, designated as Form S3. Form S3 can be characterized by data selected from: an X-ray powder diffraction pattern having peaks at 8.1, 13.6, 15.1, 16.1 and 22.6 degrees two theta ±0.2 degrees two theta; an X-ray powder diffraction pattern substantially as depicted in FIG. 14; and combinations thereof. Crystalline Form S3 of Raltegravir sodium may be further characterized by the X-ray powder diffraction pattern having additional peaks at 20.3, 23.1, 27.4, 30.2 and 32.5 degrees two theta ±0.2 degrees two theta.

As discussed above the crystalline forms of Raltegravir sodium of the present invention (namely, Form S1, Form S2 and Form S3) have advantageous properties. In particular, the crystalline forms of Raltegravir sodium of the present invention have a significantly higher dissolution rate compared with the Raltegravir potassium form I disclosed in U.S. Pat. No. 7,754,731, which lead to favourable pharmacokinetics, e.g. increased bioavailability of Raltegravir.

The present invention further comprises novel salts of Raltegravir, in particular: lithium, calcium, tert-butylamine, meglumine, diethylamine, diisopropylamine salts. The above salts can be isolated. Preferably, the above salts are in crystalline form.

In one embodiment, the present invention comprises a Raltegravir lithium salt.

In one embodiment, the present invention comprises a crystalline form of the lithium salt characterized by data selected from: an X-ray powder diffraction pattern with peaks at 10.4; 11.9; 15.6; 17.2; 20.3 degrees two theta ±0.2 degrees two theta; an X-ray powder diffraction pattern substantially as depicted in FIG. 15, and combinations thereof.

The above crystalline form of Raltegravir lithium salt can be further characterized by X-ray powder diffraction pattern having additional peaks at 8.1, 14.4, 21.3, 25.3, and 30.1 degrees two theta ±0.2 degrees two theta.

In one embodiment, the present invention comprises a crystalline form of Raltegravir calcium salt characterized by data selected from: an X-ray powder diffraction pattern with peaks at 6.5; 9.9; 18.0; 19.0 and 21.1 degrees two theta ±0.2 degrees two theta; an X-ray powder diffraction pattern substantially as depicted in FIG. 16, and combinations thereof.

In one embodiment, the present invention comprises a crystalline four of Raltegravir tert-butyl amine salt characterized by data selected from: an X-ray powder diffraction pattern with peaks at 12.4; 16.7; 17.9; 18.6 and 20.9 degrees two theta ±0.2 degrees two theta; an X-ray powder diffraction pattern with peaks at 4.2; 6.6; 8.4; 16.9 and 21.1 degrees two theta ±0.2 degrees two theta; an X-ray powder diffraction pattern substantially as depicted in FIG. 17 or 26; a solid-state $^{13}C$ NMR spectrum with signals at 121.7, 130.2, 141.6, 152.0±0.2 ppm; a solid-state $^{13}C$ NMR spectrum having chemical shifts differences between the signal exhibiting the lowest chemical shift and another in the chemical shift range of 100 to 180 ppm of 110.4, 118.9, 130.3 and 140.7±0.1 ppm; a solid-state $^{13}C$ NMR spectrum substantially as depicted in FIG. 34; and combinations thereof. The above crystalline form of Raltegravir tert-butyl amine salt can be further characterized by X-ray powder diffraction pattern having additional peaks at 9.0; 13.6; 15.0; and 22.6 degrees two theta ±0.2 degrees two theta. Alternatively, the crystalline form of Raltegravir tert-butyl amine salt as defined in any of the above data may be further characterized by XRPD pattern having additional peaks at: 9.2; 10.2; 12.6; 13.8; 15.2 and 18.0 degrees two theta ±0.2 degrees two theta.

In one embodiment, the present invention comprises a crystalline form of Raltegravir diethylamine salt characterized by data selected from: an X-ray powder diffraction pattern with peaks at 7.0; 12.6; 13.9; 17.8; 26.9 degrees two theta ±0.2 degrees two theta; an X-ray powder diffraction pattern substantially as depicted in FIG. 18, and combinations thereof. The above crystalline form of Raltegravir can be further characterized by X-ray powder diffraction having additional peaks at 10.8; 19.8; 21.6; and 23.2 degrees two theta ±0.2 degrees two theta In one embodiment, the present invention comprises a crystalline form of Raltegravir diisopropylamine salt characterized by data selected from: an X-ray powder diffraction pattern with peaks at 12.6; 16.9; 17.6; 17.9; and 21.2 degrees two theta ±0.2 degrees two theta; an X-ray powder diffraction pattern substantially as depicted in FIG. 19, and combinations thereof. The above crystalline form of Raltegravir can be further characterized by X-ray powder diffraction pattern having additional peaks at 6.2; 8.8; 19.3; 23.0; and 26.8 degrees two theta ±0.2 degrees two theta.

In one embodiment, the present invention comprises Raltegravir meglumine salt. The Raltegravir meglumine salt can be characterized by data selected from: FT Raman spectrum with peaks at: 1426.9, 850.7, 3075.3, 2945.6, 1575.7, 1426.9, 1339.1, 1052.9, 850.7, 827.8 $cm^{-1}$±2 $cm^{-1}$; FT Raman spectrum substantially as depicted in FIG. 35; and combinations thereof.

The Raltegravir meglumine may be in amorphous form. The amorphous form of Raltegravir meglumine salt can be characterized by X-ray powder diffraction pattern substantially as depicted in FIG. 36.

As discussed above, Raltegravir meglumine salt has advantageous properties. In particular, the Raltegravir meglumine of the present invention has a significantly higher dissolution rate compared with the Raltegravir potassium form I disclosed in U.S. Pat. No. 7,754,731, which lead to favourable pharmacokinetics, e.g. increased bioavailability of Raltegravir.

The present invention also describes crystalline forms of Raltegravir free hydroxy.

In one embodiment, the present invention comprises a crystalline form of Raltegravir free hydroxy, designated as Form A1. Form A1 can be characterized by data selected from: an X-ray powder diffraction pattern having peaks at 6.4, 8.3, 10.9, 12.8 and 15.6 degrees two theta ±0.2 degrees two theta; an X-ray powder diffraction pattern as depicted in FIG. 23; and combinations thereof. Crystalline Form A1 of Raltegravir free hydroxy may be further characterized by the X-ray powder diffraction pattern having additional peaks at 11.9, 13.8, 16.3, 21.7 and 23.8 degrees two theta ±0.2 degrees two theta.

In another embodiment, the present invention comprises a crystalline form of Raltegravir free hydroxy, designated as Form A2. Form A2 can be characterized by data selected from: an X-ray powder diffraction pattern having peaks at 8.1, 13.6, 15.1, 16.1, 22.6 and 23.1 degrees two theta ±0.2 degrees two theta; an X-ray powder diffraction pattern as depicted in FIG. 24; and combinations thereof. Crystalline Form A2 of Raltegravir free hydroxy may be further characterized by the X-ray powder diffraction pattern having additional peaks at 20.3, 25.5, 27.4, 30.2 and 32.5 degrees two theta ±0.2 degrees two theta.

In another embodiment, the present invention comprises a crystalline form of Raltegravir free hydroxy, designated as Form A3. Form A3 can be characterized by data selected from: an X-ray powder diffraction pattern having peaks at 7.8, 11.8, 15.5, 16.3, 23.3 and 28.5 degrees two theta ±0.2 degrees two theta; an X-ray powder diffraction pattern substantially as depicted in FIG. 25; and combinations thereof. Crystalline Form A3 of Raltegravir free hydroxy may be further characterized by the X-ray powder diffraction pattern having additional peaks at 13.5, 18.4, 22.0, 25.1, and 26.7 degrees two theta ±0.2 degrees two theta.

The above crystalline Forms of Raltegravir free hydroxy can be used to prepare Raltegravir salts such as Raltegravir potassium, for example, by reacting Raltegravir free hydroxy with a base such as potassium base, as described in U.S. Patent Application Publication No. US 2006/0122205, Example 1, step 9, or formulation thereof.

The above described salts and solid state forms of Raltegravir can be used to prepare Raltegravir potassium salt and pharmaceutical formulation thereof.

The present invention encompasses a process for preparing Raltegravir potassium comprising preparing any one of the above salts and solid state forms of Raltegravir by the processes of the present invention and converting it to Raltegravir potassium. The conversion may be done for example, by acidifying the Raltegravir salt to obtain Raltegravir free hydroxy and further reacting the formed Raltegravir free-hydroxy with a potassium base.

The present invention further encompasses 1) a pharmaceutical composition comprising any one or combination of the Raltegravir salts or of Raltegravir free-hydroxy and crystalline forms thereof, as described above, and at least one pharmaceutically acceptable excipient; and 2) the use of any one or combination of the above-described Raltegravir salts or of Raltegravir free-hydroxy and crystalline forms thereof, in the manufacture of a pharmaceutical composition, and 3) a method of treating a person suffering from HIV infection, comprising administration of an effective amount of a pharmaceutical composition comprising any one or more of the forms of Raltegravir salts or of Raltegravir free hydroxy described herein.

The pharmaceutical composition can be useful for the treatment or prophylaxis of HIV infection. The present invention also provides Raltegravir slats or Raltegravir free-hydroxy and crystalline forms thereof as described above for use as a medicament, preferably for the treatment or prophylaxis of HIV infection.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

X-Ray Powder Diffraction ("XRPD") Method:

The X-ray powder diffraction analyses of the crystalline forms of the Raltegravir salts and of the Raltegravir free-hydroxy were performed on one of two different X-ray diffractometers, giving the same results. One instrument was a Thermo ARL, Scintag X-ray powder diffractometer model X'TRA. Analyses on the Scintag diffractometer were done with a Cu-tube solid-state detector, round standard aluminum sample holder with round zero background quartz plate. Copper $K\alpha_1$ radiation ($\lambda=1.54$ Å) was used. The scanning parameters were: range: 2-40 degrees two-theta; scan mode: continuous scan; step size: 0.05 deg.; and scan rate: 3 deg/min. The other instrument was a Philips X'Pert PRO powder diffractometer. When using this instrument, sample was applied directly on silicon PW1817/32 "zero background" holder. X-Ray tube was PW3373/00; Cu anode LFF and X-ray radiation $\lambda(CuK\alpha_1)=1.54$ Å. The scanning parameters were: range: 2-40 degrees two-theta; scan mode: continuous scan; step size: 0.0167 deg.; and scan rate: 0.05 deg/sec.

The peak positions were determined by using silicon powder as internal standard in an admixture with the sample measured. The position of the silicon (111) peak was corrected to be 28.45 degrees two theta. The positions of the peaks were corrected respectively, but no corrections were performed on the diffractograms in the figures provided herein).

Differential Scanning Calorimetry ("DSC") Method:
Instrument DSC Q1000 V9.8 Build 296
Module: DSC Standard Cell RC
Pan: Aluminum standard
Gas: Nitrogen 50.0 ml/ml
Ramp: 10° C./min from 25 to 300° C.
Thermogravimetric Analysis ("TGA") Method:
Instrument AutoTGA 2950HR V5.4A
Module TGA 1000° C.
Sample size about 20 mg
Pan: Platinum
Gas1: Nitrogen 60 ml/min RAMAN Methods:
RAMAN method for measuring Raltegravir potassium form V:
Powder samples were filled into 5 mm NMR tube and Raman spectra were recorded on
Nicolet 6700 FT-IR spectrometer with NXR FT-Raman module, equipped with 1064 nm
$Nd:YVO_4$ excitation laser, $CaF_2$ beamsplitter and Ge detector.
Instrument Parameters:
Spectral range: 4000-155 $cm^{-1}$
Resolution: 4.0 $cm^{-1}$
Number of scans: 128
Laser power: 1.5 W
RAMAN method for measuring Raltegravir meglumine salt:
Instrument: MultiRam, Bruker, T. No. IRFS27, equipped with HPGe NIR detector,
Laser: 9395.2 $cm^{-1}$
Laser power: 150 mW
Resolution: 4 $cm^{-1}$
Number of scans: 20.

EXAMPLES

Reference Example

The starting Raltegravir free hydroxy and Raltegravir potassium can be prepared according to the methods described in US 2006/0122205, incorporated herein by reference.

The starting amorphous Raltegravir potassium can be prepared by dissolving Raltegravir potassium (45 g) in water (10-30 vol.) and pumping the resulting solution into spray dryer at room temperature. The inlet temperature was set to 120-130° C., and the outlet temperature 75-80° C. Alternatively, amorphous Raltegravir potassium was prepared according to the process described in example 15 below.

Example 1

Preparation of Raltegravir Potassium Form IV

A vial (20 ml) was charged with Raltegravir free hydroxy (500 mg) completely dissolved in N-methyl-pyrrolidone (NMP) (1.5 ml) at room temperature. A solution of 30% aqueous KOH (0.162 ml) was added. The mixture was stirred for 21 h at room temperature. Additional NMP (7.5 ml) was added and the mixture was stirred for an additional 6.5 h at room temperature. A solid precipitated and was filtered under reduced pressure to provide wet Raltegravir potassium crystalline Form IV. The wet product was dried overnight in a vacuum oven at 40° C. to provide Raltegravir potassium crystalline Form IV.

Example 2

Preparation of Raltegravir Potassium Form V

A vial (20 ml) was charged with Raltegravir free hydroxy (500 mg) and cyclohexane (2.5 ml) at room temperature. A solution of 30% aqueous KOH (0.162 ml) was added. An additional amount of cyclohexane (5 ml) was added. The mixture was stirred for 25 h at room temperature. A gel solid precipitated and was removed Form the mixture using a spatula and was then filtered under reduced pressure to produce wet Raltegravir potassium crystalline Form V. The product was dried overnight in a vacuum oven at 40° C. to provide raltegravir potassium crystalline Form V.

Example 3

Preparation of Raltegravir Potassium Form V

A vial (20 ml) was charged with Raltegravir potassium (300 mg) completely dissolved in distilled water (11 ml) at room temperature. The solution was concentrated using a rotary evaporator to provide wet Raltegravir potassium crystalline Form V.

Example 4

Preparation of Raltegravir Potassium Form V

A vial (20 ml) was charged with amorphous Raltegravir potassium (200 mg) and 2 drops of distilled water were added. The mixture was stirred on a rotary evaporator without vacuum for 1 h at room temperature. The product was dried overnight in a vacuum oven at 45° C. to obtain Raltegravir potassium crystalline Form V.

Example 5

Preparation of Raltegravir Potassium Form V

Amorphous Raltegravir potassium (1 g) in distilled water (1 mL) was stirred on a rotary evaporator without vacuum for 80 minutes at room temperature. The obtained product was isolated by vacuum filtration and washed with distilled water (0.75 ml). The product was dried overnight in a vacuum oven at 45° C. to obtain Raltegravir potassium crystalline Form V.

Example 6

Preparation of Raltegravir Potassium Form V

A vial (20 mL) charged with Raltegravir free Form A1 (0.5 g) and a mixture of Heptane and water (9:1, 10 vol). KOH 30% (1 eq) was added at room temperature. Seeds of Raltegravir potassium Form V were added. The thus-formed sticky slurry was stirred for 4 hours and then filtered. The thus obtained product was dried in a vacuum oven at 40° C. for overnight to obtain Raltegravir potassium crystalline Form V.

Example 7

Preparation of Raltegravir Potassium Form V

A 50 mL flask equipped with mechanical stirrer was charged with water (1 vol), KOH 85% (1 eq) and Raltegravir free Form A1 (1 g). A clear solution was obtained. Heptane (9 vol) was added at room temperature. Seeds of Raltegravir potassium Form V were added, thus forming a slurry. The slurry was stirred for 2.5 hours and then filtered; the product was dried in a vacuum oven at 40° C. for overnight to obtain Raltegravir potassium crystalline Form V.

Example 8

Preparation of Raltegravir Potassium Form V

A 50 mL flask equipped with mechanical stirrer was charged with water (1 vol), KOH 85% (1 eq) and Raltegravir free Form A1 (1 g). A clear solution was obtained. The solution was cooled in ice bath. Toluene (9 vol) was added. Seeds of Raltegravir potassium Form V were added, thus forming a slurry. The slurry was stirred for 2.5 hours and then filtered the thus obtained product was dried in a vacuum oven at 40° C. for overnight to obtain Raltegravir potassium crystalline Form V.

Example 9

Preparation of Raltegravir Potassium Form V

A 50 mL flask equipped with mechanical stirrer was charged with water (2 vol), KOH 85% (1 eq) and RLT free Form A1 (1 g). A clear solution was obtained. The solution was cooled in ice bath. Heptane (8 vol) was added; followed by addition of seeds of Raltegravir potassium Form V. The thus-formed sticky slurry was stirred for 2.5 hours and filtered. The thus obtained product was dried in a vacuum oven at 40° C. for overnight to obtain Raltegravir potassium crystalline Form V.

Example 10

Preparation of Raltegravir Potassium Form V

A 50 mL flask equipped with mechanical stirrer was charged with water (1 vol), KOH 85% (1 eq) and Raltegravir free Form A1 (1 g). A clear solution was obtained. The solution was cooled in ice bath. Heptane (9 vol), and seeds of Raltegravir potassium Form V were added. The thus formed sticky slurry was stirred for 2.5 hours and filtered. The thus obtained product was dried in a vacuum oven at 40° C. for overnight to obtain Raltegravir potassium crystalline Form V.

Example 11

Preparation of Raltegravir Potassium Form VI

A vial (20 ml) was charged with Raltegravir free hydroxy (200 mg) slurry in EtOH:H$_2$O (1000:1, 0.2 ml) at room temperature. The slurry was heated to 50° C. A solution of 45% aqueous KOH (0.044 ml) was added at 50° C. to the mixture. The resulting mixture was stirred for 5.5 h at 50° C. To this mixture was added distilled H$_2$O (1.5 ml) dropwise to produce a colorless solution. The solvent was then removed under reduced pressure to provide wet Raltegravir potassium crystalline Form VI. The product was dried in a vacuum oven at 40° C. for 3.5 hours to provide Raltegravir potassium crystalline Form VI.

Example 12

Preparation of Raltegravir Potassium Form VII

A flask (100 ml) was charged with Raltegravir free hydroxy (500 mg) completely dissolved in 1,4-dioxane (35 ml) at room temperature. A solution of 30% aqueous KOH (0.162 ml) was added. The resulting mixture was stirred for 24 h at room temperature. A solid precipitated and was filtered under reduced pressure to provide wet Raltegravir potassium crystalline Form VII.

Example 13

Preparation of Raltegravir Potassium Form VII

A vial (20 ml) was charged with amorphous Raltegravir potassium (500 mg) and dichloromethane (2.5 mL). The mixture was stirred in a sonicator for 50 minutes at room temperature. The product was filtered and then was dried overnight in a vacuum oven at 45° C. to obtain Raltegravir potassium crystalline Form VII.

Example 14

Preparation of Raltegravir Potassium Form VIII

A vial (20 ml) was charged with amorphous Raltegravir potassium (500 mg) and dry ethanol (2.5 ml) to form a slurry. The slurry was stirred for 24 h at 60° C. Dry ethanol (2.5 ml) was added and the resulting mixture was stirred for an additional 7.5 h at 60° C. The product was isolated by vacuum filtration and washed with dry ethanol (0.5 ml). The wet Raltegravir potassium was obtained as crystalline Form VIII.

Example 15

Preparation of Raltegravir Potassium Form IXa

A vial (20 ml) was charged with amorphous Raltegravir potassium (500 mg) and cyclohexane (2.5 mL) to form a mixture. The mixture was stirred for 24 hours at room temperature, and then heated to 60° C. and stirred at 60° C. for additional 24 hours. The cyclohexane evaporated overnight and therefore an additional amount of cyclohexane (2 mL) was added. The obtained product was isolated by vacuum filtration and then was dried overnight in a vacuum oven at 45° C. to obtain amorphous Raltegravir potassium. The amorphous Raltegravir potassium was heated to 250° C. at a heating rate of 10° C./min in an aluminum (standard DSC) crucible to obtain Raltegravir potassium Form IXa.

Example 16

Preparation of Raltegravir Potassium Form IXb

A vial (20 ml) was charged with amorphous Raltegravir potassium (250 mg) and placed in a closed 100 mL vessel containing cyclopentyl methyl ether (20 mL) at room temperature. The vessel was kept at room temperature for 40 days. The product was dried overnight in a vacuum oven at 45° C. to obtain Raltegravir potassium Form IXb.

Example 17

Preparation of Raltegravir Potassium Form X

A vial (20 ml) was charged with Raltegravir free hydroxy (0.5 g) and acetonitrile (7.5 mL) to obtain a solution. KOH 85% (75.6 mg) was added to the solution at room temperature. The solution was then sonicated for 40 minutes. The product was isolated by vacuum filtration to provide Raltegravir potassium Form X.

Example 18

Preparation of Raltegravir Potassium Form XI

Raltegravir potassium crystalline Form X, prepared according to example 17, was dried overnight in a vacuum oven at 45° C. to provide Raltegravir potassium crystalline Form XI.

Example 19

Preparation of Raltegravir Potassium Form XII

A 50 ml flask with magnetic stirrer was charged with Raltegravir free hydroxy (3 g, 99.66% purity, 90.73 assay). Acetonitrile (26.2 ml, 8.62 vol) was added to form a slurry. The slurry was heated to 45° C. till a clear solution was obtained. Hot filtration was done and the filtered solution was reheated to 45° C., KOH 30% solution was added dropwise (1 ml, 0.99 eq) during 15 minute (after addition of the KOH solution, precipitation was observed). The solution was cooled over 4 hour to RT, forming a slurry. The slurry was filtered and the collected product was washed with acetonitrile (1 ml). The product was dried under vacuum at 40° C. overnight to obtain Raltegravir potassium crystalline Form XII (2.7 g, 99.63% purity).

Example 20

Preparation of Raltegravir Potassium Form XIII

A vial (20 ml) was charged with Raltegravir free hydroxy (0.25 g) and pentanol (2 mL) to form a solution. KOH 85% (38 mg) was added at room temperature, forming a solution. This solution was stirred for 3 hours. The product precipitated and was isolated by centrifuge filtration. The isolated product was dried in a vacuum oven at 40° C. for 5 h to obtain Raltegravir potassium crystalline Form XIII.

Example 21

Preparation of Raltegravir Potassium Form XIV

A vial (20 ml) equipped with a magnetic stirrer was charged with Raltegravir free (250 mg) and toluene (2.5 mL). A clear solution was obtained. KOH 30% (80 μL) was added at room temperature and the reaction was stirred for five hours. A solid precipitate formed and was separated by filtration. The product was dried in a vacuum oven at 45° C. for overnight to obtain Raltegravir potassium Form XIV.

Example 22

Preparation of Raltegravir Potassium Form XV

A vial (20 ml) was charged with Raltegravir free (0.25 g) and pentanol (2 mL), forming a solution. KOH 85% (38 mg) was added at room temperature. The solution was stirred for 3 hours. The product precipitated and was isolated by centrifuge filtration. The wet sample was analyzed showed that Raltegravir potassium crystalline Form XV was obtained.

Example 23

Preparation of Raltegravir Potassium Form XV

Raltegravir free hydroxy (40 mg) was suspended in 2 mL of isopropanol, and KOH-1 g/mL (100 micro L) was added. The mixture was left on a shaker for 3 hours. Wet crystals were isolated and analyzed showing that Raltegravir potassium Form XV was obtained.

Example 24

Preparation of Raltegravir Potassium Form XVI

A 100 mL flask equipped with mechanical stirrer was charged with water (1 vol), KOH 85% (1 eq) and Raltegravir free Form A1 (5 g), and a clear solution was obtained. The solution was cooled in an ice bath. Toluene (9 vol) was added, and seeds of Raltegravir potassium Form V were added, forming a slurry. The slurry was stirred overnight and filtered to give a wet sample of Form XVI.

Example 25

Preparation of Raltegravir Sodium Form S1

A vial (20 ml) was charged with Raltegravir free hydroxy (250 mg) and acetone (6 ml). A solution of NaOH-1N (0.56 ml) was added. The resulting solution was stirred for 24 h at room temperature and then for 16 h at 4° C. Diethylether (10 ml) was added and the resulting mixture was stirred for an additional 16 h at 4° C. A solid precipitated and was filtered under reduced pressure and dried overnight in a vacuum oven at 45° C. The resulting product was analyzed by XRPD which showed a pattern of Raltegravir sodium crystalline Form S1.

Example 26

Preparation of Raltegravir Sodium Form S2

A vial (20 ml) was charged with Raltegravir free hydroxy (250 mg) and cyclohexane (5 ml). A solution of NaOH-1N (0.56 ml) was added. The resulting solution was stirred for 24 h at room temperature and a solid precipitated. The solid was filtered under reduced pressure and dried overnight in a vacuum oven at 45° C. The resulting product was analyzed by XRPD which showed a pattern of Raltegravir sodium crystalline Form S2.

Example 27

Preparation of Raltegravir Sodium Form S2

A three necked round bottom flask (100 ml) was charged with Raltegravir free hydroxy (5 g) and acetone (50 ml). A solution of NaOH-1N (11.2 ml) was added, to obtain a suspension. Heating to 40° C. led to dissolution. The solution was then cooled to room temperature and stirred. Precipitation did not occur at this point. Diethyl ether (20 ml) was added and the solution was stirred overnight during which time a solid precipitated. The solid was filtered under reduced pressure and dried overnight in a vacuum oven at 55° C. The resulting product was analyzed by XRPD which provided a pattern of Raltegravir sodium crystalline Form S2.

Example 28

Preparation of Raltegravir Sodium Form S2

A three necked round bottom flask (100 ml) was charged with Raltegravir free hydroxy (5 g) and acetonitrile (50 ml). A solution of NaOH-1N (11.2 ml) was added to obtain a suspension. Heating to 40° C. led to dissolution. The solution was cooled to room temperature and stirred. Precipitation did not occur at this point. Diethyl ether (20 ml) was added and the solution was stirred overnight during which time a solid was precipitated. The solid was filtered under reduced pressure and dried overnight in a vacuum oven at 55° C. The resulting product was analyzed by XRPD to give a pattern of Raltegravir sodium crystalline Form S2.

Example 29

Preparation of Raltegravir Sodium Form S2

A three necked round bottom flask was charged with Raltegravir free hydroxy (5 g) and ethyl acetate (50 ml). A solution of NaOH-1N (11.2 ml) was added to obtain a suspension. Heating to 40° C. led to dissolution. The solution was cooled to room temperature and stirred. Precipitation occurred and the solid was filtered after 4 hours under reduced pressure and dried overnight in a vacuum oven at 55° C. The resulting product was analyzed by XRPD which provided a pattern of Raltegravir sodium crystalline Form S2.

Example 30

Preparation of Raltegravir Sodium Form S3

A vial (20 ml) was charged with Raltegravir free hydroxy (250 mg) and methyl-formate (7.5 ml). A solution of NaOH-1N (0.56 ml) was added. The resulting solution was stirred for 24 h at room temperature and then for 16 h at 4° C. Diethylether (7.5 ml) was added and a solid was precipitated. The solid was filtered under reduced pressure and dried overnight in a vacuum oven at 45° C. The resulting product was analyzed by XRPD which provided a pattern of Raltegravir sodium crystalline Form S3.

Example 31

Preparation of Raltegravir Lithium Salt

Raltegravir free hydroxy (25.2 mg) was suspended in acetone (0.250 mL), and 1M aqueous lithium hydroxide solution (0.062 mL) was added in one portion. The mixture was shaken well and a clear solution was obtained within a few seconds. The solvent was allowed to evaporate under a flow of nitrogen and the resulting solid residue was dried at ambient temperature under vacuum for approximately 24 hours. The product was characterized by XRPD.

Example 32

Preparation of Raltegravir Calcium Salt

A physical mixture of Raltegravir free hydroxy (25.8 mg) and calcium hydroxide (~4.6 mg) was suspended in 70/30 tetrahydrofuran/water. The mixture was shaken well and the resulting suspension was temperature cycled between room temperature and 50° C. using a Heidolph shaker and incubator with a power source programmed to switch on and off every 4 hours. After approximately 72 hours, excess solvent was decanted off using a syringe and the solid residue was dried at ambient temperature under vacuum for approximately 24 hours. The product was characterised by XRPD.

Example 33

Preparation of Raltegravir T-Butylamine Salt

Raltegravir free hydroxy (24.6 mg) was suspended in ethyl acetate (0.250 mL) and tert-butylamine (6.5 µl) was added. The mixture was shaken well and the resulting suspension was temperature cycled between ambient and 50° C. using a Heidolph shaker and incubator with a power source programmed to switch on and off every 4 hours. After approximately 72 hours excess solvent was decanted off using a syringe and the solid residue was dried at ambient temperature under vacuum for approximately 24 hours. The product was characterised by XRPD.

Example 34

Preparation of Raltegravir Tert-Butylamine Salt

A three necked round bottom flask (100 ml) was charged with Raltegravir free hydroxy (5 g), iso-propyl alcohol (45 ml) and water (5 ml) to obtain a mixture. The mixture was heated to 40° C. and tert-butylamine (1300 µl) was added drop-wise. There was almost dissolution and heavy precipitation subsequently occurred. The obtained solid was filtered under reduced pressure and dried overnight in a vacuum oven at 55° C. The resulting product was characterised by XRPD.

Example 35

Preparation of Raltegravir Tert-Butylamine Salt

A three necked round bottom flask (100 ml) was charged with Raltegravir free hydroxy (5 g), ethanol (45 ml) and water (5 ml) to obtain a mixture. The mixture was heated to 40° C. and tert-butylamine (1300 µl) was added dropwise. There was almost dissolution and heavy precipitation subsequently occurred. The precipitate was filtered under reduced pressure and dried overnight in a vacuum oven at 55° C. The resulting product was characterised by XRPD.

Example 36

Preparation of Raltegravir Tert-Butylamine Salt

A three necked round bottom flask (100 ml) was charged with Raltegravir free hydroxy (5 g) and acetone (50 ml) to obtain a mixture. The mixture was heated to 40° C. and tert-butylamine (1300 µl) was added dropwise. There was dissolution and heavy precipitation subsequently occurred. The precipitate was filtered under reduced pressure and dried overnight in a vacuum oven at 55° C. The resulting product was characterised by XRPD.

Example 37

Preparation of Raltegravir Tert-Butylamine Salt

A three necked round bottom flask (100 ml) was charged with Raltegravir free hydroxy (5 g) and ethyl acetate (50 ml) to obtain a mixture. The obtained mixture was heated to 40° C. and tert-butylamine (1300 µl) was added drop-wise. There was dissolution and heavy precipitation subsequently occurred. The precipitate was filtered under reduced pressure and dried overnight in a vacuum oven at 55° C. The resulting product was characterised by XRPD.

Example 38

Preparation of Raltegravir Tert-Butylamine Salt

A three necked round bottom flask (100 ml) was charged with Raltegravir free hydroxy (5 g), ethanol (65 ml) and water (10 ml) to obtain a mixture. The obtained mixture was heated to 40° C. and a solution of tert-butylamine (1300 µl) in ethanol (2 ml) was added dropwise. After dissolution, the solution was cooled to room temperature. Precipitation occurred and the obtained solid was filtered under reduced pressure and dried overnight in a vacuum oven at 55° C. The resulting product was characterised by XRPD.

Example 39

Preparation of Raltegravir Tert-Butylamine Salt

A three necked round bottom flask (100 ml) was charged with Raltegravir free hydroxy (5 g) and acetone (75 mL) to obtain a mixture. The obtained mixture was stirred and dissolved at room temperature. tert-Butylamine (1300 µl) in acetone (2 ml) was added dropwise. Heavy precipitation occurred and the obtained solid was filtered under reduced pressure and dried overnight in a vacuum oven at 55° C. The resulting product was characterised by XRPD.

Example 40

Preparation of Raltegravir Diethylamine Salt

Raltegravir free hydroxy (24.6 mg) was suspended in ethyl acetate (0.250 mL) and diethylamine (6.4 µl) was added. The mixture was shaken well and the solid dissolved on heating. The resulting solution was temperature cycled between ambient and 50° C. using a Heidolph shaker and incubator with a power source programmed to switch on and off every 4 hours. After approximately 72 hours the solvent was allowed to evaporate under a flow of nitrogen and the solid residue was dried at ambient temperature under vacuum for approximately 24 hours. The product was characterised by XRPD.

Example 41

Preparation of Raltegravir Diisopropylamine Salt

Raltegravir free hydroxy (25.2 mg) was suspended in toluene (0.250 mL), and diisopropylamine (8.7 µl) was added to the suspension. The mixture was shaken and the resulting suspension was temperature cycled between ambient and 50° C. using a Heidolph shaker and incubator with a power source programmed to switch on and off every 4 hours. After approximately 72 hours, excess solvent was decanted off using a syringe and the solid residue was dried at ambient temperature under vacuum for approximately 24 hours. The product was characterised by XRPD.

Example 42

Preparation of Raltegravir Free Hydroxy Form A1

A solution of Raltegravir potassium (~3.4 g) in water was acidified with 2N HCl until pH 2 was obtained. The acidified solution was extracted with mixture of methyl tert-butyl ether (MTBE)/isopropyl alcohol (IPA) (400 ml/100 ml). The organic extract was evaporated to dryness. Raltegravir free hydroxy (3.1 g) was obtained as a white powder.

Example 43

Preparation of Raltegravir Free Hydroxy Form A1

A solution of Raltegravir potassium (~2 g) in water was acidified with 2N HCl until pH 2 was obtained. The acidified solution was extracted with MTBE (600 ml). The organic extract was evaporated to dryness. Raltegravir free hydroxy (1.5 g) was obtained as a white powder.

Example 44

Preparation of Raltegravir Free Hydroxy Form A2

A vial (20 ml) was charged with Raltegravir free hydroxy form A1 (500 mg) and cyclohexane (2.5 ml). The mixture was heated to 50° C. and then cooled to room temperature. Distilled water (0.159 ml) was added to the cooled mixture. The resulting mixture was stirred for 24 h at room temperature. A solid precipitated and was separated by filtration under reduced pressure to obtain Raltegravir free hydroxy crystalline Form A2. The resulting product was analyzed by XRPD to be Raltegravir free hydroxy Form A2.

Example 45

Preparation of Raltegravir Free Hydroxy Form A3

A 2 L flask with magnetic stirrer was charged with Raltegravir free hydroxy (23 g/26 g). Methanol (1600 ml, 32 vol was added and the resulting slurry was heated to reflux. A clear solution was thereby obtained. The solution was cooled slowly to RT over 8 hours to form a slurry. The slurry was filtered and the collected product was washed with methanol (20 ml). The product was then dried under vacuum at 40° C. overnight to obtain Raltegravir free hydroxy Form A3.

Example 46

Preparation of Raltegravir Potassium Form V

A 100 ml three necked round bottom flask equipped with mechanical stirrer was charged with Raltegravir free-hydroxy (2 g) and THF (15 vol., 30 mL), and a clear pinkish solution was obtained. A solution of KOH 87.7% (277 mg, 1.05 equiv.) in $H_2O$ (2 vol.) was added dropwise. The resulting clear yellow solution was cooled to 0° C. in ice bath. Seeds of Raltegravir potassium form V were added, forming a slurry. The slurry was stirred for 2.5 hours, filtered at 0° C. and the separated solid was washed with cold THF (6 ml). The obtained product was dried in a vacuum oven at 40° C. overnight to obtain Raltegravir potassium crystalline form V.

Example 47

Preparation of Raltegravir Potassium Form V

A 250 ml three necked round bottom flask equipped with mechanical stirrer was charged with Raltegravir free-hydroxy (2 g) and THF (15 vol., 30 ml), and a clear pinkish solution was obtained. A solution of KOH 87.7% (277 mg, 1.05 equiv.) in $H_2O$ (2 vol.) was added dropwise. The resulting clear yellow solution was cooled to 0° C. in ice bath. Seeds of Raltegravir potassium form V were added, forming a slurry. The slurry was stirred for 2.5 hours and filtered at 0° C. and washed with cold THF (6 ml). The product was dried in a lyophilizer to produce Raltegravir potassium crystalline form V.

Example 48

Preparation of Raltegravir Meglumine Salt

A three necked round bottom flask (50 ml) was charged with Raltegravir free hydroxy (300 mg), Meglumine (132 mg), THF (15 mL) and water (7.5 mL) to obtain a mixture. The mixture was stirred at room temperature, yellow clear solution was obtained. The solution was evaporated and dried overnight in a vacuum oven at 60° C. The resulting product was characterised by XRPD.

What is claimed is:

1. A crystalline form of Raltegravir potassium that is:
  a) crystalline Form V of Raltegravir potassium, characterized by:
    an X-ray powder diffraction pattern having peaks at 8.0, 11.9, 18.2 and 26.6 degrees two theta ±0.2 degrees two theta;
    an X-ray powder diffraction pattern substantially as depicted in FIG. 2;
    a solid-state $^{13}C$ NMR spectrum with signals at 121.9, 144.0, 149.3 and 170.3±0.2 ppm;
    a solid-state $^{13}C$ NMR spectrum having chemical shifts differences between the signal exhibiting the lowest chemical shift and another in the chemical shift range of 100 to 180 ppm of 111.9, 134.0, 139.3 and 160.3±0.1 ppm;
    a solid-state $^{13}C$ NMR spectrum substantially as depicted in FIG. 31; or combinations thereof; or
  b) crystalline Form IV of Raltegravir potassium, characterized by:
    an X-ray powder diffraction pattern having peaks at 6.5, 7.5, 8.1, 18.4 and 23.2 degrees two theta ±0.2 degrees two theta;
    an X-ray powder diffraction pattern substantially as depicted in FIG. 1; or combinations thereof.

2. The crystalline Raltegravir potassium Form V according to claim 1, characterized by:
    an X-ray powder diffraction pattern having peaks at 8.0, 11.9, 18.2 and 26.6 degrees two theta ±0.2 degrees two theta;
    an X-ray powder diffraction pattern substantially as depicted in FIG. 2;
    a solid-state $^{13}C$ NMR spectrum with signals at 121.9, 144.0, 149.3 and 170.3±0.2 ppm;
    a solid-state $^{13}C$ NMR spectrum having chemical shifts differences between the signal exhibiting the lowest chemical shift and another in the chemical shift range of 100 to 180 ppm of 111.9, 134.0, 139.3 and 160.3±0.1 ppm;
    a solid-state $^{13}C$ NMR spectrum substantially as depicted in FIG. 31; or combinations thereof.

3. The crystalline Form V of Raltegravir potassium according to claim 2; characterized by an X-ray powder diffraction pattern having peaks at 8.0, 11.9, 18.2 and 26.6 degrees two theta ±0.2 degrees two theta.

4. The crystalline Form IV of Raltegravir potassium according to claim 1, characterized by:
    an X-ray powder diffraction pattern having peaks at 6.5, 7.5, 8.1, 18.4 and 23.2 degrees two theta ±0.2 degrees two theta;
    an X-ray powder diffraction pattern substantially as depicted in FIG. 1; or combinations thereof.

5. The crystalline Raltegravir potassium Form IV according to claim 4, characterized by
    an X-ray powder diffraction pattern having peaks at 6.5, 7.5, 8.1, 18.4 and 23.2 degrees two theta ±0.2 degrees two theta, and further characterized by:
    an X-ray powder diffraction pattern having additional peaks at 13.0, 17.5, 24.2 and 25.5 degrees two theta+0.2 degrees two theta;
    a DSC thermogram as depicted in FIG. 27;
    a TGA thermogram as depicted in FIG. 28;
    or combinations thereof.

6. A pharmaceutical composition comprising the crystalline Form V or crystalline Form IV of Raltegravir potassium according to claim 1, and at least one pharmaceutically acceptable excipient.

7. The crystalline Raltegravir potassium Form V according to claim 3, further characterized by:
- an X-ray powder diffraction pattern having additional peaks at 14.9, 19.8, 24.9, 27.7 and 28.9 degrees two theta ±0.2 degrees two theta;
- a DSC thermogram substantially as depicted in FIG. 29;
- a TGA thermogram substantially as depicted in FIG. 30;
- an FT Raman spectrum substantially as depicted in FIG. 32; or combinations thereof.

* * * * *